(12) United States Patent
Lang et al.

(10) Patent No.: US 8,951,260 B2
(45) Date of Patent: Feb. 10, 2015

(54) SURGICAL CUTTING GUIDE

(75) Inventors: Philipp Lang, Lexington, MA (US);
Wolfgang Fitz, Sherborn, MA (US);
Daniel Steines, Palo Alto, CA (US);
Raymond A. Bojarski, Attleboro, MA (US)

(73) Assignee: ConforMIS, Inc., Bedford, MA (US)

( * ) Notice: Subject to any disclaimer, the term of this patent is extended or adjusted under 35 U.S.C. 154(b) by 1117 days.

(21) Appl. No.: 12/139,324

(22) Filed: Jun. 13, 2008

(65) Prior Publication Data

US 2008/0275452 A1 Nov. 6, 2008

Related U.S. Application Data

(60) Provisional application No. 60/943,726, filed on Jun. 13, 2007.

(51) Int. Cl.
*A61B 17/58* (2006.01)
*A61B 17/60* (2006.01)
*A61B 19/00* (2006.01)
*A61B 5/103* (2006.01)
*A61B 17/00* (2006.01)
*A61B 17/15* (2006.01)
*A61B 5/00* (2006.01)
*A61B 17/17* (2006.01)

(52) U.S. Cl.
CPC ............... *A61B 17/15* (2013.01); *A61B 19/50* (2013.01); *A61B 5/103* (2013.01); *A61B 2017/00526* (2013.01); *A61B 17/157* (2013.01); *A61B 5/4528* (2013.01); *A61B 2019/303* (2013.01); *A61B 2019/304* (2013.01); *A61B 17/1764* (2013.01)
USPC .......................................................... 606/88

(58) Field of Classification Search
USPC ...................................... 606/86 R, 87–89, 96
See application file for complete search history.

(56) References Cited

U.S. PATENT DOCUMENTS 3,314,420 A 4/1967 Smith et al. ..................... 128/92
3,605,123 A 9/1971 Hahn .................................. 3/1
(Continued)

FOREIGN PATENT DOCUMENTS

DE 2306552 8/1974 ................ A61F 1/00
DE 3516743 11/1986 ................ A61F 2/36
(Continued)

OTHER PUBLICATIONS

United States Patent and Trademark Office, Office Action dated Oct. 20, 2010, pertaining to U.S. Appl. No. 12/135,719, 10 pages.
(Continued)

*Primary Examiner* — Matthew Lawson
(74) *Attorney, Agent, or Firm* — Sunstein Kann Murphy & Timbers LLP

(57) ABSTRACT

The present invention is directed to a surgical cutting guide for guiding a surgical instrument along a cutting path located on a biological tissue. The surgical guide includes a contact surface that conforms to a surface associated with the tissue and at least one guide for restricting movement of a surgical instrument in a first direction and for allowing the movement of the surgical instrument in a second direction along a cutting path across the surface of the tissue. The guide further contains a stop for restricting movement of the surgical instrument in the second direction along the cutting path. The stop is based at least, in part, on patient specific information.

20 Claims, 4 Drawing Sheets

(56) References Cited

U.S. PATENT DOCUMENTS

| | | | |
|---|---|---|---|
| 3,798,679 A | 3/1974 | Ewald | 3/1 |
| 3,808,606 A | 5/1974 | Tronzo | 3/1 |
| 3,843,975 A | 10/1974 | Tronzo | 3/1 |
| 3,855,638 A | 12/1974 | Pillar | 3/1 |
| 3,938,198 A | 2/1976 | Kahn et al. | 3/1.912 |
| 3,987,499 A | 10/1976 | Scharbach et al. | 3/1.91 |
| 4,052,753 A | 10/1977 | Dedo | 3/1 |
| 4,055,862 A | 11/1977 | Farling | 3/1.91 |
| 4,085,466 A | 4/1978 | Goodfellow et al. | 3/1.91 |
| 4,098,626 A | 7/1978 | Graham et al. | 149/19.4 |
| 4,203,444 A | 5/1980 | Bonnell et al. | 128/276 |
| 4,213,816 A | 7/1980 | Morris | 156/245 |
| 4,340,978 A | 7/1982 | Buechel et al. | 3/1.911 |
| 4,368,040 A | 1/1983 | Weissman | 433/36 |
| 4,436,684 A | 3/1984 | White | 264/138 |
| 4,501,266 A | 2/1985 | McDaniel | 128/69 |
| 4,502,161 A | 3/1985 | Wall | 3/1.91 |
| 4,586,496 A | 5/1986 | Keller | 128/92 E |
| 4,594,380 A | 6/1986 | Chapin et al. | 524/144 |
| 4,601,290 A | 7/1986 | Effron et al. | 128/305 |
| 4,609,551 A | 9/1986 | Caplan et al. | 424/95 |
| 4,627,853 A | 12/1986 | Campbell et al. | 623/16 |
| 4,715,860 A | 12/1987 | Amstutz et al. | 623/22 |
| 4,721,104 A | 1/1988 | Kaufman et al. | 128/92 |
| 4,759,350 A | 7/1988 | Dunn et al. | 128/92 VW |
| 4,769,040 A | 9/1988 | Wevers | 623/20 |
| 4,841,975 A | 6/1989 | Woolson | 128/653 |
| 4,846,835 A | 7/1989 | Grande | 623/11 |
| 4,865,607 A | 9/1989 | Witzel et al. | 623/20 |
| 4,880,429 A | 11/1989 | Stone | 623/18 |
| 4,886,258 A | 12/1989 | Scott | 269/328 |
| 4,936,862 A | 6/1990 | Walker et al. | 623/23 |
| 4,979,949 A | 12/1990 | Matsen, III et al. | 606/53 |
| 5,007,936 A | 4/1991 | Woolson | 623/23 |
| 5,041,138 A | 8/1991 | Vacanti et al. | 623/16 |
| 5,053,039 A | 10/1991 | Hofmann et al. | 606/87 |
| 5,059,216 A | 10/1991 | Winters | 623/20 |
| 5,067,964 A | 11/1991 | Richmond et al. | 623/18 |
| 5,122,144 A | 6/1992 | Bert et al. | 606/88 |
| 5,129,908 A | 7/1992 | Petersen | 606/88 |
| 5,133,759 A | 7/1992 | Turner | 623/20 |
| 5,154,717 A | 10/1992 | Matsen, III et al. | 606/53 |
| 5,162,430 A | 11/1992 | Rhee et al. | 525/54.1 |
| 5,171,322 A | 12/1992 | Kenny | 623/18 |
| 5,197,985 A | 3/1993 | Caplan et al. | 623/16 |
| 5,206,023 A | 4/1993 | Hunziker | 424/423 |
| 5,226,914 A | 7/1993 | Caplan et al. | 623/16 |
| 5,234,433 A | 8/1993 | Bert et al. | 606/88 |
| 5,246,530 A | 9/1993 | Bugle et al. | 156/643 |
| 5,250,050 A | 10/1993 | Poggie et al. | 606/79 |
| 5,258,032 A | 11/1993 | Bertin | 623/20 |
| 5,270,300 A | 12/1993 | Hunziker | 514/12 |
| 5,288,797 A | 2/1994 | Khalil et al. | 524/872 |
| 5,299,288 A | 3/1994 | Glassman et al. | 395/80 |
| 5,303,148 A | 4/1994 | Mattson et al. | 364/413.01 |
| 5,306,311 A | 4/1994 | Stone et al. | 623/18 |
| 5,314,482 A | 5/1994 | Goodfellow et al. | 623/20 |
| 5,344,459 A | 9/1994 | Swartz | 623/18 |
| 5,360,446 A | 11/1994 | Kennedy | 623/16 |
| 5,368,858 A | 11/1994 | Hunziker | 424/423 |
| 5,380,332 A | 1/1995 | Ferrante | 606/79 |
| 5,387,216 A | 2/1995 | Thornhill et al. | 606/86 |
| 5,403,319 A | 4/1995 | Matsen, III et al. | 606/88 |
| 5,437,676 A | 8/1995 | Bouraly et al. | 606/88 |
| 5,468,787 A | 11/1995 | Braden et al. | 523/113 |
| 5,474,559 A | 12/1995 | Bertin et al. | 606/89 |
| 5,478,739 A | 12/1995 | Slivka et al. | 435/240.23 |
| 5,486,180 A | 1/1996 | Dietz et al. | 606/87 |
| 5,501,687 A | 3/1996 | Willert et al. | 606/94 |
| 5,503,162 A | 4/1996 | Athanasiou et al. | 128/774 |
| 5,523,843 A | 6/1996 | Yamane et al. | 356/363 |
| 5,540,696 A | 7/1996 | Booth, Jr. et al. | 606/88 |
| 5,542,947 A | 8/1996 | Treacy | 606/88 |
| 5,554,190 A | 9/1996 | Draenert | 623/16 |
| 5,556,432 A | 9/1996 | Kubein-Meesenburg et al. | 623/20 |
| 5,571,205 A | 11/1996 | James | 623/24 |
| 5,575,793 A | 11/1996 | Carls et al. | 606/80 |
| 5,578,037 A | 11/1996 | Sanders et al. | 606/80 |
| 5,593,450 A | 1/1997 | Scott et al. | 623/20 |
| 5,597,379 A | 1/1997 | Haines et al. | 606/80 |
| 5,601,563 A | 2/1997 | Burke et al. | 606/86 |
| 5,613,970 A | 3/1997 | Houston et al. | 606/88 |
| 5,616,146 A | 4/1997 | Murray | 606/80 |
| 5,630,820 A | 5/1997 | Todd | 606/90 |
| 5,632,745 A | 5/1997 | Schwartz | 606/75 |
| 5,649,929 A | 7/1997 | Callaway | 606/88 |
| 5,658,290 A | 8/1997 | Lechot | 606/80 |
| 5,671,741 A | 9/1997 | Lang et al. | 128/653.2 |
| 5,681,316 A | 10/1997 | DeOrio et al. | 606/88 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,684,562 A | 11/1997 | Fujieda | 351/212 |
| 5,688,282 A | 11/1997 | Baron et al. | 606/90 |
| 5,728,162 A | 3/1998 | Eckhoff | 623/20 |
| 5,735,277 A | 4/1998 | Schuster | 128/653.1 |
| 5,749,874 A | 5/1998 | Schwartz | 606/75 |
| 5,749,876 A | 5/1998 | Duvillier et al. | 606/88 |
| 5,766,259 A | 6/1998 | Sammarco | 623/21 |
| 5,768,134 A | 6/1998 | Swaelens et al. | 364/468.28 |
| 5,769,899 A | 6/1998 | Schwartz et al. | 623/18 |
| 5,776,137 A | 7/1998 | Katz | 606/88 |
| 5,786,217 A | 7/1998 | Tubo et al. | 435/402 |
| 5,795,353 A | 8/1998 | Felt | 623/18 |
| 5,800,438 A | 9/1998 | Tuke et al. | 606/90 |
| 5,827,289 A | 10/1998 | Reiley et al. | 606/86 |
| 5,830,216 A | 11/1998 | Insall et al. | 606/88 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,860,981 A | 1/1999 | Bertin et al. | 606/89 |
| 5,871,018 A | 2/1999 | Delp et al. | 128/898 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia, III et al. | 364/578 |
| 5,885,296 A | 3/1999 | Masini | 606/86 |
| 5,885,297 A | 3/1999 | Matsen, III | 606/87 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,934 A | 5/1999 | Grande et al. | 435/325 |
| 5,911,723 A | 6/1999 | Ashby et al. | 606/88 |
| 5,916,220 A | 6/1999 | Masini | 606/88 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,972,385 A | 10/1999 | Liu et al. | 424/486 |
| 5,995,738 A | 11/1999 | DiGioia, III et al. | 395/500.32 |
| 6,001,895 A | 12/1999 | Harvey et al. | 523/113 |
| 6,002,859 A | 12/1999 | DiGioia, III et al. | 395/500.32 |
| 6,007,537 A | 12/1999 | Burkinshaw et al. | 606/66 |
| 6,010,509 A | 1/2000 | Delgado et al. | 606/88 |
| 6,013,103 A | 1/2000 | Kaufman et al. | 623/20 |
| 6,046,379 A | 4/2000 | Stone et al. | 623/11 |
| 6,056,754 A | 5/2000 | Haines et al. | 606/80 |
| 6,056,756 A | 5/2000 | Eng et al. | 606/87 |
| 6,057,927 A | 5/2000 | Lévesque et al. | 356/432 T |
| 6,077,270 A | 6/2000 | Katz | 606/88 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,096,043 A | 8/2000 | Techiera et al. | 606/88 |
| 6,102,916 A | 8/2000 | Masini | 606/88 |
| 6,106,529 A | 8/2000 | Techiera | 606/88 |
| 6,110,209 A | 8/2000 | Stone | 623/16.11 |
| 6,120,541 A | 9/2000 | Johnson | 623/14.12 |
| 6,126,690 A | 10/2000 | Ateshian et al. | 623/18 |
| 6,139,578 A | 10/2000 | Lee et al. | 623/16.11 |

(56) References Cited

U.S. PATENT DOCUMENTS

| | | | |
|---|---|---|---|
| 6,156,069 A | 12/2000 | Amstutz | 623/22.11 |
| 6,161,080 A | 12/2000 | Aouni-Ateshian et al. | 703/11 |
| 6,187,010 B1 | 2/2001 | Masini | 606/86 |
| 6,200,606 B1 | 3/2001 | Peterson et al. | 424/574 |
| 6,203,546 B1 | 3/2001 | MacMahon | 606/87 |
| 6,203,576 B1 | 3/2001 | Afriat et al. | 623/20.27 |
| 6,205,411 B1 | 3/2001 | DiGioia, III et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,251,143 B1 | 6/2001 | Schwartz et al. | 623/23.72 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,296,646 B1 | 10/2001 | Williamson | 606/90 |
| 6,299,905 B1 | 10/2001 | Peterson et al. | 424/486 |
| 6,322,588 B1 | 11/2001 | Ogle et al. | 623/1.46 |
| 6,328,765 B1 | 12/2001 | Hardwick et al. | 623/23.72 |
| 6,344,043 B1 | 2/2002 | Pappas | 606/96 |
| 6,344,059 B1 | 2/2002 | Krakovits et al. | 623/20.31 |
| 6,352,558 B1 | 3/2002 | Spector | 623/18.11 |
| 6,358,253 B1 | 3/2002 | Torrie et al. | 606/96 |
| 6,365,405 B1 | 4/2002 | Salzmann et al. | 435/366 |
| 6,371,958 B1 | 4/2002 | Overaker | 606/72 |
| 6,373,250 B1 | 4/2002 | Tsoref et al. | 324/309 |
| 6,375,658 B1 | 4/2002 | Hangody et al. | 606/80 |
| 6,379,367 B1 | 4/2002 | Vibe-Hansen et al. | 606/151 |
| 6,382,028 B1 | 5/2002 | Wooh et al. | 73/602 |
| 6,383,228 B1 | 5/2002 | Schmotzer | 623/23.35 |
| 6,387,131 B1 | 5/2002 | Miehlke et al. | 623/20.15 |
| 6,429,013 B1 | 8/2002 | Halvorsen et al. | 435/377 |
| 6,443,988 B2 | 9/2002 | Felt et al. | 623/17.12 |
| 6,443,991 B1 | 9/2002 | Running | 623/20.27 |
| 6,444,222 B1 | 9/2002 | Asculai et al. | 424/484 |
| 6,459,948 B1 | 10/2002 | Ateshian et al. | 700/117 |
| 6,468,314 B2 | 10/2002 | Schwartz et al. | 623/23.72 |
| 6,478,799 B1 | 11/2002 | Williamson | 606/90 |
| 6,479,996 B1 | 11/2002 | Hoogeveen et al. | 324/309 |
| 6,510,334 B1 | 1/2003 | Schuster et al. | 600/407 |
| 6,520,964 B2 | 2/2003 | Tallarida et al. | 396/567 |
| 6,558,421 B1 | 5/2003 | Fell et al. | 623/14.12 |
| 6,560,476 B1 | 5/2003 | Pelletier et al. | 600/410 |
| 6,575,980 B1 | 6/2003 | Robie et al. | 606/88 |
| 6,589,281 B2 | 7/2003 | Hyde, Jr. | 623/18.11 |
| 6,620,168 B1 | 9/2003 | Lombardo et al. | 606/88 |
| 6,626,945 B2 | 9/2003 | Simon et al. | 623/17.19 |
| 6,626,948 B2 | 9/2003 | Storer et al. | 623/23.14 |
| 6,632,225 B2 | 10/2003 | Sanford et al. | 606/87 |
| 6,632,235 B2 | 10/2003 | Weikel et al. | 606/192 |
| 6,652,587 B2 | 11/2003 | Felt et al. | 623/20.16 |
| 6,673,077 B1 | 1/2004 | Katz | 606/88 |
| 6,673,116 B2 | 1/2004 | Reiley | 623/21.18 |
| 6,679,917 B2 | 1/2004 | Ek | 623/20.14 |
| 6,702,821 B2 | 3/2004 | Bonutti | 606/88 |
| 6,712,856 B1 * | 3/2004 | Carignan et al. | 623/20.35 |
| 6,875,218 B2 | 4/2005 | Dye et al. | 606/91 |
| 6,905,514 B2 | 6/2005 | Carignan et al. | 623/20.35 |
| 6,916,341 B2 | 7/2005 | Rolston | 623/20.3 |
| 6,928,742 B2 | 8/2005 | Broers et al. | 33/512 |
| 6,969,393 B2 | 11/2005 | Pinczewski et al. | 606/88 |
| 6,984,249 B2 | 1/2006 | Keller | 623/20.24 |
| 7,008,430 B2 | 3/2006 | Dong et al. | 606/80 |
| 7,060,074 B2 | 6/2006 | Rosa et al. | 606/88 |
| 7,104,997 B2 | 9/2006 | Lionberger et al. | 606/88 |
| 7,115,131 B2 | 10/2006 | Engh et al. | 606/79 |
| 7,117,027 B2 | 10/2006 | Zheng et al. | 600/426 |
| 7,141,053 B2 | 11/2006 | Rosa et al. | 606/86 |
| 7,184,814 B2 | 2/2007 | Lang et al. | 600/416 |
| 7,239,908 B1 | 7/2007 | Alexander et al. | 600/427 |
| 7,245,697 B2 | 7/2007 | Lang | 378/54 |
| 7,282,054 B2 | 10/2007 | Steffensmeier et al. | 606/96 |
| 7,292,674 B2 | 11/2007 | Lang | 378/54 |
| 7,379,529 B2 | 5/2008 | Lang | 378/54 |
| 7,442,196 B2 | 10/2008 | Fisher et al. | 606/88 |
| 7,467,892 B2 | 12/2008 | Lang et al. | 378/207 |
| 7,468,075 B2 | 12/2008 | Lang et al. | 623/16.11 |
| 7,534,263 B2 | 5/2009 | Burdulis, Jr. et al. | 623/14.12 |
| 7,603,192 B2 | 10/2009 | Martin et al. | 700/98 |
| 7,615,054 B1 | 11/2009 | Bonutti | 606/88 |
| 7,618,451 B2 | 11/2009 | Berez et al. | 623/14.12 |
| 7,695,477 B2 | 4/2010 | Creger et al. | 606/87 |
| 7,747,305 B2 | 6/2010 | Dean et al. | 600/407 |
| 7,806,896 B1 | 10/2010 | Bonutti | 606/86 R |
| 7,833,275 B2 | 11/2010 | Mears et al. | 623/22.11 |
| 7,881,768 B2 | 2/2011 | Lang et al. | 600/407 |
| 7,981,158 B2 | 7/2011 | Fitz et al. | 128/92 |
| 7,983,777 B2 | 7/2011 | Melton et al. | 700/98 |
| 8,036,729 B2 | 10/2011 | Lang et al. | 600/407 |
| 8,062,302 B2 | 11/2011 | Lang et al. | 606/87 |
| 8,066,708 B2 | 11/2011 | Lang et al. | 606/88 |
| 8,070,752 B2 | 12/2011 | Metzger et al. | 606/88 |
| 8,083,745 B2 | 12/2011 | Lang et al. | 606/87 |
| 8,092,462 B2 | 1/2012 | Pinczewski et al. | 606/88 |
| 8,105,330 B2 | 1/2012 | Fitz et al. | 606/88 |
| 8,109,942 B2 | 2/2012 | Carson | 606/130 |
| 8,112,142 B2 | 2/2012 | Alexander et al. | 600/407 |
| 8,122,582 B2 | 2/2012 | Burdulis, Jr. et al. | 29/527.1 |
| 8,123,753 B2 | 2/2012 | Poncet | 606/87 |
| RE43,282 E | 3/2012 | Alexander et al. | 600/427 |
| 8,160,345 B2 | 4/2012 | Pavlovskaia et al. | 382/131 |
| 8,167,888 B2 | 5/2012 | Steffensmeier | 606/88 |
| 8,221,430 B2 | 7/2012 | Park et al. | 606/88 |
| 8,234,097 B2 | 7/2012 | Steines et al. | 703/1 |
| 8,257,360 B2 | 9/2012 | Richard et al. | 606/88 |
| 8,265,730 B2 | 9/2012 | Alexander et al. | 600/410 |
| 8,282,646 B2 | 10/2012 | Schoenefeld et al. | 606/88 |
| 8,306,601 B2 | 11/2012 | Lang et al. | 600/407 |
| 8,311,306 B2 | 11/2012 | Pavlovskaia et al. | 382/131 |
| 8,337,501 B2 | 12/2012 | Fitz et al. | 606/86 R |
| 8,337,503 B2 | 12/2012 | Lian | 606/87 |
| 8,337,507 B2 | 12/2012 | Lang et al. | 606/102 |
| 8,343,218 B2 | 1/2013 | Lang et al. | 623/16.11 |
| 8,357,166 B2 | 1/2013 | Aram et al. | 606/88 |
| 8,361,076 B2 | 1/2013 | Roose et al. | 606/88 |
| 8,366,771 B2 | 2/2013 | Burdulis, Jr. et al. | 623/14.12 |
| 8,369,926 B2 | 2/2013 | Lang et al. | 600/407 |
| 8,377,066 B2 | 2/2013 | Katrana et al. | 606/86 R |
| 8,377,068 B2 | 2/2013 | Aker et al. | 606/87 |
| 8,377,073 B2 | 2/2013 | Wasielewski | 606/102 |
| 8,377,129 B2 | 2/2013 | Fitz et al. | 623/14.12 |
| 8,380,471 B2 | 2/2013 | Iannotti et al. | 703/6 |
| 8,398,646 B2 | 3/2013 | Metzger et al. | 606/88 |
| 8,407,067 B2 | 3/2013 | Uthgenannt et al. | 705/2 |
| 8,419,740 B2 | 4/2013 | Aram et al. | 606/88 |
| 8,425,524 B2 | 4/2013 | Aker et al. | 606/88 |
| 8,439,926 B2 | 5/2013 | Bojarski et al. | 606/88 |
| 8,460,304 B2 | 6/2013 | Fitz et al. | 606/88 |
| 8,480,754 B2 | 7/2013 | Bojarski et al. | 623/20.35 |
| 8,500,740 B2 | 8/2013 | Bojarski et al. | 606/86 R |
| 8,529,568 B2 | 9/2013 | Bouadi | 606/84 |
| 8,529,630 B2 | 9/2013 | Bojarski et al. | 623/20.14 |
| 8,545,569 B2 | 10/2013 | Fitz et al. | 623/20.14 |
| 8,551,099 B2 | 10/2013 | Lang et al. | 606/86 R |
| 8,551,102 B2 | 10/2013 | Fitz et al. | 606/88 |
| 8,551,103 B2 | 10/2013 | Fitz et al. | 606/88 |
| 8,551,169 B2 | 10/2013 | Fitz et al. | 623/14.12 |
| 8,556,906 B2 | 10/2013 | Fitz et al. | 606/87 |
| 8,556,907 B2 | 10/2013 | Fitz et al. | 606/87 |
| 8,556,971 B2 | 10/2013 | Lang | 623/14.12 |
| 8,556,983 B2 | 10/2013 | Bojarski et al. | 623/20.35 |
| 8,561,278 B2 | 10/2013 | Fitz et al. | 29/407.09 |
| 8,562,611 B2 | 10/2013 | Fitz et al. | 606/80 |
| 8,562,618 B2 | 10/2013 | Fitz et al. | 606/88 |
| 8,568,479 B2 | 10/2013 | Fitz et al. | 623/14.12 |
| 8,568,480 B2 | 10/2013 | Fitz et al. | 623/14.12 |
| 8,617,172 B2 | 12/2013 | Fitz et al. | 606/88 |
| 8,617,242 B2 | 12/2013 | Philipp | 623/16.11 |
| 8,623,026 B2 | 1/2014 | Wong et al. | 606/96 |
| 8,634,617 B2 | 1/2014 | Tsougarakis et al. | 382/128 |
| 8,638,998 B2 | 1/2014 | Steines et al. | 382/128 |

(56) References Cited

U.S. PATENT DOCUMENTS

| | | | |
|---|---|---|---|
| 8,641,716 B2 | 2/2014 | Fitz et al. | 606/80 |
| 8,657,827 B2 | 2/2014 | Fitz et al. | 606/87 |
| 8,682,052 B2 | 3/2014 | Fitz et al. | 382/131 |
| 8,690,945 B2 | 4/2014 | Fitz et al. | 623/16.11 |
| 8,709,089 B2 | 4/2014 | Lang et al. | 623/18.11 |
| 8,735,773 B2 | 5/2014 | Lang | 219/121.72 |
| 8,768,028 B2 | 7/2014 | Lang et al. | 382/131 |
| 8,771,365 B2 | 7/2014 | Bojarski et al. | 623/20.32 |
| 2001/0001120 A1 | 5/2001 | Masini | 606/86 |
| 2001/0010023 A1 | 7/2001 | Schwartz et al. | 623/23.72 |
| 2001/0039455 A1 | 11/2001 | Simon et al. | 623/23.51 |
| 2002/0013626 A1 | 1/2002 | Geistlich et al. | 623/23.57 |
| 2002/0029038 A1 | 3/2002 | Haines | 606/54 |
| 2002/0045940 A1 | 4/2002 | Giannetti et al. | 623/11.11 |
| 2002/0059049 A1 | 5/2002 | Bradbury et al. | 703/11 |
| 2002/0068979 A1 | 6/2002 | Brown et al. | 623/20.3 |
| 2002/0072821 A1 | 6/2002 | Baker | 700/98 |
| 2002/0079601 A1 | 6/2002 | Russell et al. | 264/40.1 |
| 2002/0082703 A1 | 6/2002 | Repicci | 623/20.29 |
| 2002/0087274 A1 | 7/2002 | Alexander et al. | 702/19 |
| 2002/0106625 A1 | 8/2002 | Hung et al. | 435/1.1 |
| 2002/0115647 A1 | 8/2002 | Halvorsen et al. | 514/171 |
| 2002/0120274 A1 | 8/2002 | Overaker et al. | 606/72 |
| 2002/0120281 A1 | 8/2002 | Overaker | 606/151 |
| 2002/0127264 A1 | 9/2002 | Felt et al. | 424/423 |
| 2002/0133230 A1 | 9/2002 | Repicci | 623/14.12 |
| 2002/0143402 A1 | 10/2002 | Steinberg | 623/22.16 |
| 2002/0151986 A1 | 10/2002 | Asculai et al. | 424/484 |
| 2002/0173852 A1 | 11/2002 | Felt et al. | 623/20.32 |
| 2002/0183850 A1 | 12/2002 | Felt et al. | 623/20.16 |
| 2003/0028196 A1 | 2/2003 | Bonutti | 606/87 |
| 2003/0055500 A1 | 3/2003 | Fell et al. | 623/14.12 |
| 2003/0055501 A1 | 3/2003 | Fell et al. | 623/14.12 |
| 2003/0055502 A1 | 3/2003 | Lang et al. | 623/16.11 |
| 2003/0060882 A1 | 3/2003 | Fell et al. | 623/14.12 |
| 2003/0060883 A1 | 3/2003 | Fell et al. | 623/14.12 |
| 2003/0060884 A1 | 3/2003 | Fell et al. | 623/14.12 |
| 2003/0060885 A1 | 3/2003 | Fell et al. | 623/14.12 |
| 2003/0069591 A1 | 4/2003 | Carson et al. | 606/130 |
| 2003/0100907 A1 | 5/2003 | Rosa et al. | 606/86 |
| 2003/0100953 A1 | 5/2003 | Rosa et al. | 623/20.3 |
| 2003/0120347 A1 | 6/2003 | Steinberg | 623/22.17 |
| 2003/0158558 A1 | 8/2003 | Horn | 606/87 |
| 2003/0158606 A1 | 8/2003 | Coon et al. | 623/20.15 |
| 2003/0163137 A1 | 8/2003 | Smucker et al. | 606/87 |
| 2003/0173695 A1 | 9/2003 | Monkhouse et al. | 264/40.1 |
| 2003/0216669 A1 | 11/2003 | Lang et al. | 600/587 |
| 2003/0225457 A1 | 12/2003 | Justin et al. | 623/20.14 |
| 2003/0236521 A1 | 12/2003 | Brown et al. | 606/80 |
| 2004/0098133 A1 | 5/2004 | Carignan et al. | 623/20.35 |
| 2004/0102852 A1 | 5/2004 | Johnson et al. | 623/20.15 |
| 2004/0102866 A1 | 5/2004 | Harris et al. | 700/117 |
| 2004/0122521 A1 | 6/2004 | Lee et al. | 623/20.15 |
| 2004/0133276 A1 | 7/2004 | Lang et al. | 623/14.12 |
| 2004/0138754 A1 | 7/2004 | Lang et al. | 623/20.14 |
| 2004/0147927 A1 | 7/2004 | Tsougarakis et al. | 606/53 |
| 2004/0153079 A1 | 8/2004 | Tsougarakis et al. | 606/77 |
| 2004/0153162 A1 | 8/2004 | Sanford et al. | 623/20.3 |
| 2004/0153164 A1 | 8/2004 | Sanford et al. | 623/20.29 |
| 2004/0167390 A1 | 8/2004 | Alexander et al. | 600/410 |
| 2004/0167630 A1 | 8/2004 | Rolston | 623/20.14 |
| 2004/0193280 A1 | 9/2004 | Webster et al. | 623/20.33 |
| 2004/0204644 A1 | 10/2004 | Tsougarakis et al. | 600/410 |
| 2004/0204760 A1 | 10/2004 | Fitz et al. | 623/14.12 |
| 2004/0236424 A1 | 11/2004 | Berez et al. | 623/14.12 |
| 2004/0249386 A1 | 12/2004 | Faoro | 606/88 |
| 2005/0015153 A1 | 1/2005 | Goble et al. | 623/23.46 |
| 2005/0021039 A1 | 1/2005 | Cusick et al. | 606/88 |
| 2005/0043807 A1 | 2/2005 | Wood | 623/20.14 |
| 2005/0055028 A1 | 3/2005 | Haines | 606/79 |
| 2005/0085920 A1 | 4/2005 | Williamson | 623/20.14 |
| 2005/0107883 A1 | 5/2005 | Goodfried et al. | 623/20.15 |
| 2005/0107884 A1 | 5/2005 | Johnson et al. | 623/20.15 |
| 2005/0107886 A1 | 5/2005 | Crabtree et al. | 623/20.24 |
| 2005/0119664 A1 | 6/2005 | Carignan et al. | 606/96 |
| 2005/0143745 A1 | 6/2005 | Hodorek et al. | 606/87 |
| 2005/0148843 A1 | 7/2005 | Roose | 600/407 |
| 2005/0171545 A1 | 8/2005 | Walsh et al. | 606/72 |
| 2005/0171612 A1 | 8/2005 | Rolston | 623/20.19 |
| 2005/0192588 A1 | 9/2005 | Garcia | 606/88 |
| 2005/0216305 A1 | 9/2005 | Funderud | 705/2 |
| 2005/0234461 A1 | 10/2005 | Burdulis, Jr. et al. | 606/79 |
| 2005/0267584 A1 | 12/2005 | Burdulis et al. | 623/20.19 |
| 2005/0278034 A1 | 12/2005 | Johnson et al. | 623/20.15 |
| 2006/0052795 A1 | 3/2006 | White | 606/102 |
| 2006/0069318 A1 | 3/2006 | Keaveny et al. | 600/300 |
| 2006/0111722 A1 | 5/2006 | Bouadi | 606/79 |
| 2006/0122616 A1 | 6/2006 | Bennett et al. | 606/87 |
| 2006/0149283 A1 | 7/2006 | May et al. | 606/96 |
| 2006/0200162 A1 | 9/2006 | Farling et al. | 606/88 |
| 2006/0235421 A1 | 10/2006 | Rosa et al. | 606/88 |
| 2007/0015995 A1 | 1/2007 | Lang | 600/407 |
| 2007/0073305 A1 | 3/2007 | Lionberger et al. | 606/87 |
| 2007/0118141 A1 | 5/2007 | Marchyn et al. | 606/88 |
| 2007/0198022 A1 | 8/2007 | Lang et al. | 606/88 |
| 2007/0203430 A1 | 8/2007 | Lang et al. | 600/587 |
| 2007/0226986 A1 | 10/2007 | Park et al. | 29/592 |
| 2007/0233141 A1 | 10/2007 | Park et al. | 606/88 |
| 2007/0233151 A1 | 10/2007 | Chudik | 606/96 |
| 2007/0233156 A1 | 10/2007 | Metzger | 606/130 |
| 2007/0255288 A1 | 11/2007 | Mahfouz et al. | 606/102 |
| 2007/0276224 A1 | 11/2007 | Lang et al. | 600/410 |
| 2007/0276501 A1 | 11/2007 | Betz et al. | 623/17.16 |
| 2007/0288030 A1 | 12/2007 | Metzger et al. | 606/87 |
| 2007/0293868 A1 | 12/2007 | Delfosse et al. | 606/88 |
| 2008/0004709 A1 | 1/2008 | O'Neill et al. | 623/20.35 |
| 2008/0015433 A1 | 1/2008 | Alexander et al. | 600/427 |
| 2008/0021566 A1 | 1/2008 | Peters et al. | 623/20.16 |
| 2008/0025463 A1 | 1/2008 | Lang | 378/54 |
| 2008/0031412 A1 | 2/2008 | Lang et al. | 378/54 |
| 2008/0058613 A1 | 3/2008 | Lang et al. | 600/300 |
| 2008/0058945 A1 | 3/2008 | Hajaj et al. | 623/20.14 |
| 2008/0114370 A1 | 5/2008 | Shoenefeld | 606/96 |
| 2008/0147072 A1 | 6/2008 | Park et al. | 606/87 |
| 2008/0170659 A1 | 7/2008 | Lang et al. | 378/56 |
| 2008/0195216 A1 | 8/2008 | Philipp | 623/18.11 |
| 2008/0215059 A1 | 9/2008 | Carignan et al. | 606/96 |
| 2008/0219412 A1 | 9/2008 | Lang | 378/207 |
| 2008/0243127 A1 | 10/2008 | Lang et al. | 606/87 |
| 2008/0255445 A1 | 10/2008 | Neubauer et al. | 600/416 |
| 2008/0262624 A1 | 10/2008 | White et al. | 623/20.32 |
| 2008/0275452 A1 | 11/2008 | Lang et al. | 606/88 |
| 2008/0281328 A1 | 11/2008 | Lang et al. | 606/87 |
| 2008/0281329 A1 | 11/2008 | Lang et al. | 606/87 |
| 2008/0281426 A1 | 11/2008 | Fitz et al. | 623/17.16 |
| 2008/0319448 A1 | 12/2008 | Lavallee et al. | 606/102 |
| 2009/0024131 A1 | 1/2009 | Metzger et al. | 606/88 |
| 2009/0076371 A1 | 3/2009 | Lang et al. | 600/407 |
| 2009/0087276 A1 | 4/2009 | Rose | 409/79 |
| 2009/0088753 A1 | 4/2009 | Aram et al. | 606/79 |
| 2009/0088758 A1 | 4/2009 | Bennett | 606/82 |
| 2009/0099567 A1 | 4/2009 | Zajac | 606/79 |
| 2009/0110498 A1 | 4/2009 | Park | 408/1 R |
| 2009/0131941 A1* | 5/2009 | Park et al. | 606/87 |
| 2009/0131942 A1 | 5/2009 | Aker et al. | 606/88 |
| 2009/0138020 A1 | 5/2009 | Park et al. | 606/88 |
| 2009/0151736 A1 | 6/2009 | Belcher et al. | 128/898 |
| 2009/0222014 A1 | 9/2009 | Bojarski et al. | 606/88 |
| 2009/0226068 A1 | 9/2009 | Fitz et al. | 382/131 |
| 2009/0254093 A1 | 10/2009 | White et al. | 606/89 |
| 2009/0307893 A1 | 12/2009 | Burdulis, Jr. et al. | 29/527.1 |
| 2009/0326666 A1 | 12/2009 | Wyss et al. | 623/20.29 |
| 2010/0049195 A1 | 2/2010 | Park et al. | 606/87 |
| 2010/0082035 A1 | 4/2010 | Keefer | 606/97 |
| 2010/0087829 A1 | 4/2010 | Metzger et al. | 606/96 |
| 2010/0152741 A1 | 6/2010 | Park et al. | 606/89 |
| 2010/0160917 A1 | 6/2010 | Fitz et al. | 606/88 |
| 2010/0168754 A1 | 7/2010 | Fitz et al. | 606/88 |
| 2010/0256479 A1 | 10/2010 | Park et al. | 600/410 |
| 2010/0274534 A1 | 10/2010 | Steines et al. | 703/1 |
| 2010/0281678 A1 | 11/2010 | Burdulis, Jr. et al. | 29/592 |
| 2010/0298894 A1 | 11/2010 | Bojarski et al. | 606/86 R |
| 2010/0303313 A1 | 12/2010 | Lang et al. | 382/128 |
| 2010/0305573 A1 | 12/2010 | Fitz et al. | 606/87 |

(56) References Cited

U.S. PATENT DOCUMENTS

| | | | |
|---|---|---|---|
| 2010/0305574 A1 | 12/2010 | Fitz et al. | 606/88 |
| 2010/0332194 A1 | 12/2010 | McGuan et al. | 703/1 |
| 2011/0029093 A1 | 2/2011 | Bojarski et al. | 623/20.35 |
| 2011/0040387 A1 | 2/2011 | Ries et al. | 623/20.27 |
| 2011/0066193 A1 | 3/2011 | Lang et al. | 606/86 R |
| 2011/0071533 A1 | 3/2011 | Metzger et al. | 606/88 |
| 2011/0071581 A1 | 3/2011 | Lang et al. | 606/86 R |
| 2011/0125009 A1 | 5/2011 | Lang et al. | 600/425 |
| 2011/0166578 A1 | 7/2011 | Stone et al. | 606/88 |
| 2011/0213368 A1 | 9/2011 | Fitz et al. | 606/80 |
| 2011/0213373 A1 | 9/2011 | Fitz et al. | 606/87 |
| 2011/0213374 A1 | 9/2011 | Fitz et al. | 606/87 |
| 2011/0213377 A1 | 9/2011 | Lang et al. | 606/89 |
| 2011/0213427 A1 | 9/2011 | Fitz et al. | 606/86 R |
| 2011/0213428 A1 | 9/2011 | Fitz et al. | 606/86 R |
| 2011/0213429 A1 | 9/2011 | Lang et al. | 606/86 R |
| 2011/0213430 A1 | 9/2011 | Lang et al. | 606/86 R |
| 2011/0213431 A1 | 9/2011 | Fitz et al. | 606/86 R |
| 2011/0218539 A1 | 9/2011 | Fitz et al. | 606/87 |
| 2011/0218542 A1 | 9/2011 | Lian | 606/88 |
| 2011/0218545 A1 | 9/2011 | Catanzarite et al. | 606/96 |
| 2011/0218584 A1 | 9/2011 | Fitz et al. | 606/86 R |
| 2011/0230888 A1 | 9/2011 | Lang et al. | 606/87 |
| 2011/0238073 A1 | 9/2011 | Lang et al. | 606/89 |
| 2011/0295329 A1 | 12/2011 | Fitz et al. | 606/86 R |
| 2011/0313423 A1 | 12/2011 | Lang et al. | 606/87 |
| 2011/0319897 A1 | 12/2011 | Lang et al. | 606/79 |
| 2011/0319900 A1 | 12/2011 | Lang et al. | 606/87 |
| 2012/0029520 A1 | 2/2012 | Lang et al. | 606/89 |
| 2012/0041446 A1 | 2/2012 | Wong et al. | 606/96 |
| 2012/0066892 A1 | 3/2012 | Lang et al. | 29/592 |
| 2012/0071881 A1 | 3/2012 | Lang et al. | 606/87 |
| 2012/0071882 A1 | 3/2012 | Lang et al. | 606/88 |
| 2012/0071883 A1 | 3/2012 | Lang et al. | 606/88 |
| 2012/0072185 A1 | 3/2012 | Lang et al. | 703/1 |
| 2012/0078598 A1 | 3/2012 | McDaniel | 703/6 |
| 2012/0101503 A1 | 4/2012 | Lang et al. | 606/87 |
| 2012/0123422 A1 | 5/2012 | Agnihotri et al. | 606/89 |
| 2012/0141034 A1 | 6/2012 | Iannotti et al. | 382/199 |
| 2012/0143197 A1 | 6/2012 | Lang et al. | 606/87 |
| 2012/0151730 A1 | 6/2012 | Fitz et al. | 29/407.01 |
| 2012/0158001 A1 | 6/2012 | Burdulis, Jr. et al. | 606/88 |
| 2012/0197260 A1 | 8/2012 | Fitz et al. | 606/88 |
| 2012/0209394 A1 | 8/2012 | Bojarski et al. | 623/20.32 |
| 2012/0239045 A1 | 9/2012 | Li | 606/86 |
| 2012/0265496 A1 | 10/2012 | Mahfouz | 703/1 |
| 2012/0276509 A1 | 11/2012 | Iannotti et al. | 434/267 |
| 2012/0289966 A1 | 11/2012 | Fitz et al. | 606/88 |
| 2012/0296337 A1 | 11/2012 | Fitz et al. | 606/80 |
| 2012/0310364 A1 | 12/2012 | Li et al. | 623/23.55 |
| 2012/0316564 A1 | 12/2012 | Serbousek et al. | 606/80 |
| 2012/0323246 A1 | 12/2012 | Catanzarite et al. | 606/88 |
| 2013/0006250 A1 | 1/2013 | Metzger et al. | 606/87 |
| 2013/0018379 A1 | 1/2013 | Fitz et al. | 606/88 |
| 2013/0018380 A1 | 1/2013 | Fitz et al. | 623/14.12 |
| 2013/0018464 A1 | 1/2013 | Fitz et al. | 606/88 |
| 2013/0024000 A1 | 1/2013 | Bojarski et al. | 623/20.14 |
| 2013/0030419 A1 | 1/2013 | Fitz et al. | 606/1 |
| 2013/0030441 A1 | 1/2013 | Fitz et al. | 606/87 |
| 2013/0035766 A1 | 2/2013 | Meridew | 623/22.21 |
| 2013/0066321 A1 | 3/2013 | Mannss et al. | 606/88 |
| 2013/0079781 A1 | 3/2013 | Fitz et al. | 606/80 |
| 2013/0079876 A1 | 3/2013 | Fitz et al. | 623/14.12 |
| 2013/0081247 A1 | 4/2013 | Fitz et al. | 29/407.09 |
| 2013/0096562 A1 | 4/2013 | Fitz et al. | 606/88 |
| 2013/0103363 A1 | 4/2013 | Lang et al. | 703/1 |
| 2013/0119579 A1 | 5/2013 | Iannotti et al. | 264/256 |
| 2013/0123792 A1 | 5/2013 | Fitz et al. | 606/96 |
| 2013/0184713 A1 | 7/2013 | Bojarski et al. | 606/88 |
| 2013/0211409 A1 | 8/2013 | Burdulis, Jr. et al. | 606/88 |
| 2013/0253522 A1 | 9/2013 | Bojarski et al. | 606/88 |
| 2013/0289570 A1 | 10/2013 | Chao | 606/88 |
| 2013/0296874 A1 | 11/2013 | Chao | 606/88 |
| 2013/0317511 A1 | 11/2013 | Bojarski et al. | 606/102 |
| 2013/0331850 A1 | 12/2013 | Bojarski et al. | 606/102 |
| 2014/0031826 A1 | 1/2014 | Bojarski et al. | 606/87 |
| 2014/0058396 A1 | 2/2014 | Fitz et al. | 606/87 |
| 2014/0058397 A1 | 2/2014 | Fitz et al. | 606/88 |
| 2014/0066935 A1 | 3/2014 | Fitz et al. | 606/87 |
| 2014/0066936 A1 | 3/2014 | Fitz et al. | 606/87 |
| 2014/0074441 A1 | 3/2014 | Fitz et al. | 703/1 |
| 2014/0163568 A1 | 6/2014 | Wong et al. | 606/96 |
| 2014/0188240 A1 | 7/2014 | Lang et al. | 623/22.12 |
| 2014/0208578 A1 | 7/2014 | Linderman et al. | 29/592 |

FOREIGN PATENT DOCUMENTS

| | | | |
|---|---|---|---|
| DE | 44 34 539 | 4/1996 | A61F 2/38 |
| DE | 20303498 | 7/2003 | A61B 17/15 |
| DE | 20303498 | 8/2003 | A61B 17/15 |
| EP | 0337901 | 10/1989 | A61B 17/14 |
| EP | 0528080 | 2/1993 | A61F 2/30 |
| EP | 0 704 193 | 4/1996 | A61F 2/30 |
| EP | 0626156 | 7/1997 | A61F 2/38 |
| EP | 0613380 | 12/1999 | A61L 27/00 |
| EP | 0993807 | 4/2000 | A61B 17/17 |
| EP | 1074229 | 2/2001 | A61F 2/38 |
| EP | 1077253 | 2/2001 | C12N 5/00 |
| EP | 1120087 | 8/2001 | A61B 17/06 |
| EP | 1129675 | 9/2001 | A61F 2/30 |
| EP | 1132061 | 9/2001 | A61F 2/28 |
| EP | 0732091 | 12/2001 | A61F 2/38 |
| EP | 0896825 | 7/2002 | A61L 27/00 |
| EP | 0814731 | 8/2002 | A61F 2/30 |
| EP | 1234552 | 8/2002 | A61F 2/00 |
| EP | 1234555 | 8/2002 | A61F 2/30 |
| EP | 0809987 | 10/2002 | A61F 2/38 |
| EP | 0833620 | 10/2002 | A61K 9/22 |
| EP | 0530804 | 6/2004 | A61L 25/00 |
| FR | 2819714 | 7/2002 | A61F 2/44 |
| FR | 2918554 | 1/2009 | A61B 17/17 |
| GB | 1451283 | 9/1976 | A61F 1/24 |
| GB | 2291355 | 1/1996 | A61F 2/38 |
| GB | 2348373 | 10/2000 | A61F 2/38 |
| JP | 1-249049 | 10/1989 | A61F 2/38 |
| JP | 8-173465 | 7/1996 | A61F 2/38 |
| JP | 9-206322 | 8/1997 | A61F 2/38 |
| JP | 2002-102236 | 4/2002 | A61B 17/16 |
| WO | WO 87/02882 | 5/1987 | A61F 2/38 |
| WO | WO 90/09769 | 9/1990 | A61F 2/28 |
| WO | WO 93/04710 | 3/1993 | A61L 25/00 |
| WO | WO 93/09819 | 5/1993 | A61L 27/00 |
| WO | WO 93/25157 | 12/1993 | A61B 17/57 |
| WO | WO 95/27450 | 10/1995 | A61F 2/38 |
| WO | WO 95/28688 | 10/1995 | G06T 15/00 |
| WO | WO 95/30390 | 11/1995 | A61F 2/38 |
| WO | WO 95/32623 | 12/1995 | A01N 1/02 |
| WO | WO 96/24302 | 8/1996 | A61B 17/90 |
| WO | WO 97/25942 | 7/1997 | A61F 2/32 |
| WO | WO 97/26847 | 7/1997 | A61F 2/44 |
| WO | WO 97/27885 | 8/1997 | A61L 27/00 |
| WO | WO 97/38676 | 10/1997 | A61K 9/10 |
| WO | WO 98/12994 | 4/1998 | A61F 2/28 |
| WO | WO 98/20816 | 5/1998 | A61F 2/38 |
| WO | WO 98/30617 | 7/1998 | C08G 63/12 |
| WO | WO 98/32384 | 7/1998 | A61B 17/58 |
| WO | WO 99/02654 | 1/1999 | C12N 5/00 |
| WO | WO 99/08598 | 2/1999 | A61B 8/00 |
| WO | WO 99/08728 | 2/1999 | A61L 27/00 |
| WO | WO 99/40864 | 8/1999 | A61B 17/56 |
| WO | WO 99/42061 | 8/1999 | A61F 2/38 |
| WO | WO 99/47186 | 9/1999 | A61L 27/00 |
| WO | WO 99/51719 | 10/1999 | C12M 3/00 |
| WO | WO 99/56674 | 11/1999 | A61F 2/36 |
| WO | WO 00/09179 | 2/2000 | A61L 25/00 |
| WO | WO 00/15153 | 3/2000 | A61F 2/38 |
| WO | WO 00/19911 | 4/2000 | A61B 17/02 |
| WO | WO 00/35346 | 6/2000 | A61B 5/11 |
| WO | WO 00/48550 | 8/2000 | |
| WO | WO 00/59411 | 10/2000 | A61F 2/38 |
| WO | WO 00/74554 | 12/2000 | |
| WO | WO 01/10356 | 2/2001 | A61F 2/46 |
| WO | WO 01/17463 | 3/2001 | A61F 2/30 |
| WO | WO 01/19254 | 3/2001 | A61B 17/00 |

(56) References Cited

FOREIGN PATENT DOCUMENTS

| WO | WO 01/35968 | 5/2001 | ............ | A61K 35/00 |
|---|---|---|---|---|
| WO | WO 01/45764 | 6/2001 | ............ | A61L 27/36 |
| WO | WO 01/66021 | 9/2001 | ............ | A61B 17/14 |
| WO | WO 01/68800 | 9/2001 | ............ | C12M 3/00 |
| WO | WO 01/70142 | 9/2001 | ............ | A61F 2/38 |
| WO | WO 01/91672 | 12/2001 | ............ | A61F 2/36 |
| WO | WO 02/00270 | 1/2002 | ............ | A61L 27/14 |
| WO | WO 02/00275 | 1/2002 | ............ | A61L 31/14 |
| WO | WO 02/02158 | 1/2002 | ............ | A61L 27/14 |
| WO | WO 02/22013 | 3/2002 | ............ | A61B 5/055 |
| WO | WO 02/22014 | 3/2002 | ............ | A61B 5/055 |
| WO | WO 02/23483 | 3/2002 | ............ | G06T 11/00 |
| WO | WO 02/34310 | 5/2002 | ............ | A61L 31/04 |
| WO | WO 02/36147 | 5/2002 | ............ | A61K 31/04 |
| WO | WO 02/061688 | 8/2002 | ............ | G06T 17/00 |
| WO | WO 02/096268 | 12/2002 | | |
| WO | WO 03/007788 | 1/2003 | | |
| WO | WO 03/037192 | 5/2003 | ............ | A61B 17/15 |
| WO | WO 03/047470 | 6/2003 | ............ | A61F 2/34 |
| WO | WO 03/051210 | 6/2003 | ............ | A61B 17/58 |
| WO | WO 03/055400 | 7/2003 | ............ | A61B 17/74 |
| WO | WO 2004/043305 | 5/2004 | ............ | A61F 2/30 |
| WO | WO 2004/049981 | 6/2004 | ............ | A61F 2/46 |
| WO | WO 2005/051239 | 6/2005 | ............ | A61F 2/08 |
| WO | WO 2005/051240 | 6/2005 | ............ | A61F 2/08 |
| WO | WO 2006/060795 | 6/2006 | ............ | A61B 17/17 |
| WO | WO 2006/127283 | 11/2006 | ............ | A61B 17/17 |
| WO | WO 2007/041375 | 4/2007 | ............ | A61F 2/38 |
| WO | WO 2007/092841 | 8/2007 | ............ | A61B 17/15 |
| WO | WO 2008/112996 | 9/2008 | ............ | A61B 17/15 |
| WO | WO 2008/117028 | 10/2008 | ............ | A61B 17/15 |
| WO | WO 2008/157412 | 12/2008 | ............ | A61B 17/17 |
| WO | WO 2009/001083 | 12/2008 | ............ | A61B 17/15 |
| WO | WO 2009/009660 | 1/2009 | ............ | A61F 2/30 |
| WO | WO 2009/106366 | 9/2009 | ............ | A61B 17/15 |
| WO | WO 2009/106816 | 9/2009 | ............ | A61B 19/00 |
| WO | WO 2009/111639 | 9/2009 | ............ | A61B 17/58 |
| WO | WO 2010/121147 | 10/2010 | ............ | A61B 17/90 |
| WO | WO 2010/148103 | 12/2010 | ............ | A61B 17/17 |
| WO | WO 2011/059641 | 5/2011 | ............ | A61B 17/15 |
| WO | WO 2011/130421 | 10/2011 | ............ | A61B 17/56 |
| WO | WO 2012/021241 | 2/2012 | ............ | A61B 17/88 |
| WO | WO 2012/021846 | 2/2012 | ............ | A61B 17/90 |
| WO | WO 2012/021894 | 2/2012 | ............ | A61F 2/46 |
| WO | WO 2012/021895 | 2/2012 | ............ | A61F 2/46 |
| WO | WO 2012/027150 | 3/2012 | ............ | G06F 19/00 |
| WO | WO 2012/051542 | 4/2012 | ............ | A61B 17/16 |
| WO | WO 2012/112694 | 8/2012 | ............ | A61B 6/00 |
| WO | WO 2012/112698 | 8/2012 | ............ | A61F 2/30 |
| WO | WO 2012/112701 | 8/2012 | ............ | A61F 2/30 |
| WO | WO 2012/112702 | 8/2012 | ............ | A61F 2/30 |
| WO | WO 2013/119865 | 8/2013 | ............ | A61B 17/90 |

OTHER PUBLICATIONS

Sunstein Kann Murphy & Timbers LLP, Response to Office Action dated Aug. 26, 2010, pertaining to U.S. Appl. No. 12/361,213, 22 pages.
United States Patent and Trademark Office, Office Action dated Feb. 28, 2011, pertaining to U.S. Appl. No. 12/048,764, 12 pages.
European Patent Office, Extended European Search Report—European Application No. 10181743.5-2310, dated Mar. 11, 2011, 6 pages.
Portheine, F., Radermacher K., Zimolong, A., et al, "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Radermacher, Klaus, Helmholtz Institute of Biomedical Technology, "Computer-Assisted Planning and Execution of Orthopedic Surgery Using Individual Surgical Templates", May 18, 1999.
Radermacher, Klaus, German Version: Helmholtz Institute of Biomedical Technology, "Computer-Assisted Planning and Execution of Orthopedic Surgery Using Individual Surgical Templates", May 18, 1999.
Radermacher, Klaus, "Computer Assisted Orthopaedic Surgery With Image Based Individual Templates" Clinical Orthopaedics, Sep. 1998, vol. 354, pp. 28-38.
Radermacher, K., Protheine, F., Zimolong, A., et al, "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.
Radermacher, K., Rau, G., Staudte, HW, "Computer Integrated Orthopedic Surgery—Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher, K., Staudte HW, Rau, G., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher, K., Staudte HW, Rau, G., "CT Image Based Planning and Execution of Interventions in Orthopedic Surgery Using Individual Templates—Experimental Results and Aspects of Clinical Applications." In Nolte LP, Ganz, R. (eds). CAOS—Computer Assisted Orthopaedic Surgery. Bern, Hans Huber (In Press) 1998.
International Searching Authority, International Search Report—International Application No. PCT/US03/38158, dated Feb. 23, 2005, 6 pages.
European Patent Office, European Search Report—Application No. EP 03790194, dated Jul. 6, 2006, 5 pages.
International Searching Authority, International Search Report—International Application No. PCT/US2005/044008, dated Mar. 30, 2006, together with the Written Opinion of the International Searching Authority, 12 pages.
International Searching Authority, International Search Report—International Application No. PCT/US2007/061681, dated Sep. 7, 2007, together with the Written Opinion of the International Searching Authority, 12 pages.
International Bureau, International Preliminary Report on Patentability—International Application No. PCT/US2005/044008, dated Jun. 14, 2007, together with the Written Opinion of the International Searching Authority, 8 pages.
United States Patent and Trademark Office, Office Action dated Jun. 15, 2007, pertaining to U.S. Appl. No. 09/882,363, 9 pages.
Bromberg & Sunstein LLP, Response to Office Action dated Jun. 15, 2007, pertaining to U.S. Appl. No. 09/882,363, 12 pages.
United States Patent and Trademark Office, Office Action dated Mar. 21, 2008, pertaining to U.S. Appl. No. 09/882,363, 12 pages.
Bromberg and Sunstein LLP, Response to Office Action dated Jan. 30, 2007, pertaining to U.S. Appl. No. 09/882,363, 7 pages.
International Searching Authority, International Search Report—International Application No. PCT/US2008/057045, dated Jul. 15, 2008, together with the Written Opinion of the International Searching Authority, 9 pages.
International Searching Authority, Invitation to Pay Additional Fees, and Where Applicable, Protest Fee—International Application No. PCT/US2008/066994, dated Oct. 21, 2008, 5 pages.
Birnbaum et al., "Computer-Assisted Orthopedic Surgery With Individual Templates and Comparison to Conventional Operation Method", Spine, vol. 26, No. 4, pp. 365-369, Feb. 2001.
Chelule et al., "Computer Aided Design of Personalized Jigs in Total Knee Replacement", 3$^{rd}$ Annual Meeting of CAOS Int'l Proc., Spain, Jun. 18, 21, 2003, pp. 58-59.
Froemel et al., "Computer Assisted Template Based Navigation for Total Knee Replacement", Documents presented at CAOS on Jun. 17, 2001, 4 pages.
Hafez et al., "Computer Assisted Total Knee Replacement: Could a Two-Piece Custom Template Replace the Complex Conventional Instrumentations?", 4$^{th}$ Annual Meeting of CAOS Int'l Proc., Chicago, Jun. 16-19, 2004, pp. 63-64.
Hafez et al., "Computer-Assisted Total Hip Arthroplasty: The Present and the Future", Future Rheumatol., vol. 1, pp. 121-131, 2006.

(56) References Cited

OTHER PUBLICATIONS

Portheine et al., In German: "Potentials of CT-based Planning and Template-based Procedure in Hip and Knee Surgery", Orth. Prac., vol. 36, pp. 786-791, 2000.
Portheine et al., English Translation with Certification: "Potentials of CT-based Planning and Template-based Procedure in Hip and Knee Surgery", Orth. Prac., vol. 36, pp. 786-791, 2000.
Portheine, In German: "Model-Based Operation Planning in Orthopedic Surgery", Thesis, RWTH Aachen University, Apr. 22, 2004, 90 pages.
Portheine, English Translation with Certification: "Model-Based Operation Planning in Orthopedic Surgery", Thesis, RWTH Aachen University, Apr. 22, 2004, 170 pages.
Radermacher et al., "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al., "Computer Assisted Matching of Planning and Execution in Orthopedic Surgery", IEEE, EMBS, San Diego, 1993, pp. 946-947.
Radermacher, "Computer Assisted Matching of Planning and Execution in Orthopedic Surgery", Slide Presentation, San Diego, Nov. 29, 1993, 22 pages.
Radermacher et al., "Computer Integrated Advanced Orthopedics (CIAO)", $2^{nd}$ European Conference on Eng. and Med., presented Apr. 26, 1993, 12 pages.
Radermacher et al., "Surgical Therapy Technology", Helmholtz-Institut Aachen Research Report, 1993-1994, pp. 189-219.
Radermacher, "Image Guided Orthopedic Surgery with Individual Templates", Helmhotz-Institute for Biomed. Eng., 2 pages, 1997.
Radermacher et al., In German: "Computer-assisted operative interventions in orthopedics—are there prospects for endoprosthetics as well?", Prac. Ortho., vol. 27, pp. 149-164, 1997.
Radermacher et al., English Translation with Certification: "Computer-assisted operative interventions in orthopedics—are there prospects for endoprosthetics as well?", Prac. Ortho., vol. 27, pp. 1-17, 1997.
Radermacher et al., "Computer Based Decision Support for the Planning of Contact Faces for Manual Registration with Individual Templates", Helmholtz-Institute for Biomed. Eng., 7 pages, 1997-98.
Radermacher, In German: "Computer-Based Decision Support in the Selection and Evaluation of Contact Surfaces for Manual Referencing", Lecture presented at Helmholtz Meeting '98 and OSS '98, 7 pages.
Radermacher, English Translation with Certification: "Computer-Based Decision Support in the Selection and Evaluation of Contact Surfaces for Manual Referencing", Lecture presented at Helmholtz Meeting '98 and OSS '98, 8 pages.
Radermacher et al., In German: "Computer-Assisted Planning and Operation in Orthopedics", Orth. Prac. $36^{th}$ year, pp. 731-737, Dec. 2000.
Radermacher et al., English Translation with Certification: "Computer-Assisted Planning and Operation in Orthopedics", Orth. Prac. $36^{th}$ year, pp. 731-737, Dec. 2000.
Radermacher, "Template Based Navigation—An Efficient Technique for Hip and Knee Surgery", CAOS First Asian Meet, India, Mar. 27-28, 2004, pp. 44-50.
Rau et al., "Small and Neat", Medical Tech. Int'l, pp. 65, 67 and 69, 1993-1994.
Schkommadau et al., "Clinical Application of Individual Templates for Pedicle Screw Placement in Comparison to Computer Navigation", Poster presented at CAOS, Feb. 18, 2000, 1 page.
Schkommadau et al., In German: "Clinical Experience With the Individual Template Technique", Orth. Prac., vol. 37, No. 1, pp. 19-22, 2001.
Schkommadau et al., English Translation with Certification: "Clinical Experience With the Individual Template Technique", Orth. Prac., vol. 37, No. 1, pp. 19-22, 2001.

Seel et al., "Three-Dimensional Planning and Virtual Radiographs in Revision Total Hip Arthroplasty for Instability", Clinical Orthopaedics and Related Research, No. 442, pp. 35-38, Jan. 2006.
Staudte et al., In German: "Computer-Assisted Operation Planning and Technique in Orthopedics", North Rhine-Westphalia Acad. for Sciences, Lecture N.444, ISSN 0944-8799, 2000, 17 pages.
Staudte et al., English Translation with Certification: "Computer-Assisted Operation Planning and Technique in Orthopedics", North Rhine-Westphalia Acad. for Sciences, Lecture N.444, ISSN 0944-8799, 2000, 34 pages.
European Patent Office, European Search Report—Application No. 09716738.1 dated Feb. 6, 2012, 10 pages.
European Patent Office, Extended European Search Report—Application No. 10181149.5-1526 dated Apr. 19, 2012, 9 pages.
European Patent Office, Extended European Search Report—Application No. 10181198.2-1526 dated Apr. 19, 2012, 9 pages.
United States Patent and Trademark Office, Office Action dated Jan. 13, 2012 pertaining to U.S. Appl. No. 12/776,840, 10 pages.
United States Patent and Trademark Office, Office Action dated May 31, 2012, pertaining to U.S. Appl. No. 12/398,753, 7 pages.
United States Patent and Trademark Office, Office Action dated Jun. 5, 2012, pertaining to U.S. Appl. No. 12/776,984, 7 pages.
Brandt et al., In German: "CRIGOS—Development of a Compact Robot System for Image-Guided Orthopedic Surgery," Der Orthopäde, Springer-Verlag, vol. 29, No. 7, pp. 645-649 (Jul. 2000).
Brandt et al., English Translation with Certification: "CRIGOS—Development of a Compact Robot System for Image-Guided Orthopedic Surgery," Der Orthopäde, Springer-Verlag, vol. 29, No. 7, pp. 645-649 (Jul. 2000).
CAOS, "MIS meets CAOS Spring 2005 Symposium Schedule", CAOS Spring 2005 Symposium, pp. 1-9, May 19, 2005.
Chelule et al., "Patient-Specific Template to Preserve Bone Stock in Total Knee Replacement: Preliminary Results", $15^{th}$ Annual ISTA Symposium, Sep. 2002, 1 page.
Hafez et al., "Computer Assisted Total Knee Replacement: Could a Two-Piece Custom Template Replace the Complex Conventional Instrumentations?" Session 6: Novel Instruments; Computer Aided Surgery, Session 6, vol. 9, No. 3, pp. 93-94 (Jun. 2004).
Hafez et al., "Computer-assisted Total Knee Arthroplasty Using Patient-specific Templating," Clinical Orthopaedics and Related Research, No. 444, pp. 184-192 (Mar. 2006).
Radermacher et al., "Computer Assisted Orthopedic Surgery by Means of Individual Templates • Aspects and Analysis of Potential Applications•" Proceedings of the First International Symposium on Medical Robotics and Computer Assisted Surgery, vol. 1: Sessions I-III, MRCAS '94, Pittsburgh, PA, pp. 42-48 (Sep. 22-24, 1994).
Schiffers et al., In German: "Planning and execution of orthopedic surgery using individualized templates," Der Orthopäde, Springer-Verlag, vol. 29, No. 7, pp. 636-640, (Jul. 2000).
Schiffers et al., English Translation with Certification: "Planning and execution of orthopedic surgery using individualized templates," Der Orthopäde, Springer-Verlag, vol. 29, No. 7, pp. 636-640, (Jul. 2000).
Thoma et al., In German: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., In German: "Custom-made knee endoprosthetics using subtraction data of three-dimensional CT scans—A new approach," Der Orthopäde, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," Der Orthopäde, Springer-Verlag, vol. 29, No. 7, pp. 641-644, (Jul. 2000).
United States Patent and Trademark Office, Office Action dated Apr. 20, 2011, pertaining to U.S. Appl. No. 12/135,612, 13 pages.
United States Patent and Trademark Office, Office Action dated Sep. 26, 2011 pertaining to U.S. Appl. No. 12/048,764, 9 pages.

(56) References Cited

OTHER PUBLICATIONS

United States Patent and Trademark Office, Office Action dated Oct. 23, 2009, pertaining to U.S. Appl. No. 10/764,010, 13 pages.
United States Patent and Trademark Office, Office Action dated Jan. 9, 2009, pertaining to U.S. Appl. No. 10/764,010 11 pages.
Bromberg & Sunstein LLP, Response to Office Action dated Jan. 9, 2009, pertaining to U.S. Appl. No. 10/764,010, 25 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10,764,010, 21 pages.
United States Patent and Trademark Office, Notice of Allowance dated Dec. 16, 2010, pertaining to U.S. Appl. No. 10/764,010, 11 pages.
United States Patent and Trademark Office, Notice of Allowance dated Aug. 5, 2011, pertaining to U.S. Appl. No. 10/764,010, 14 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
Andersson et al., "MacIntosh Arthroplasty in Rheumatoid Arthritis," Acta. Orthrop. Scand. 45(2):245-259 (1974).
Argenson et al., "Is There a Place for Patellofemoral Arthroplasty?," Clinical Orthopaedics and Related Research No. 321, pp. 162-167 (1995).
Blum et al., "Knee Arthroplasty in Patients with Rheumatoid Arthritis," ANN. Rheum. Dis. 33 (1): 1-11 (1974).
Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).
Brown, Ph.D., et al., "MRI Basic Principles and Applications", Second Ed., Mark A. Brown and Richard C. Semelka, 1999, Wiley-Liss Inc., Title Page and Table of Contents Pages Only (ISBN 0471330620).
Cameron, et al., "Review of a Failed Knee Replacement and Some Observations on the Design of a Knee Resurfacing Prosthesis," Arch. Orthop Trauma Surg. 97(2):87-89 (1980).
Carr et al., "Surface Interpolation with Radial Basis Functions for Medical Imaging," IEEE Transactions on Medical Imaging, IEEE, Inc. New York, vol. 16, pp. 96-107 (Feb. 1997).
Clary et al., "Experience with the MacIntosh Knee Prosthesis," South Med. J. 65(3):265-272 (1972).
Conaty, et al., "Surgery of the Hip and Knee in Patients with Rheumatoid Arthritis," J. Bone Joint Surg. Am. 55(2):301-314 (1973).
DeWinter et al., "The Richards Type II Patellofemoral Arthroplasty", Acta Orthop Scand 2001; 72 (5):487-490.
Delp et al., "A Graphics-Based Software System to Develop and Analyze Models of Musculoskeletal Structures," Comput. Biol. Med., vol. 25, No. 1, pp. 21-34, 1995.
Farrar et al., "Computed Tomography Scan Scout Film for Measurement of Femoral Axis in Knee Arthroplasty," J. Arthroplasty, vol. 14, No. 8, pp. 1030-1031, 1999.
Ghelman et al., "Kinematics of the Knee After Prosthetic Replacements", Clin. Orthop. May 1975: (108):149-157.
Hastings et al., "Double Hemiarthroplasty of the Knee in Rheumatoid Arthritis, A Survey of Fifty Consecutive Cases," J. Bone Joint Surg. Br. 55(1):112-118 (1973).
Henderson et al., "Experience with the Use of the Macintosh Prosthesis in Knees of Patients with Pheumatoid Arthritis," South. Med. J. 62(11):1311-1315 (1969).
Jessop et al., "Follow-up of the MacIntosh Arthroplasty of the Knee Joint," Rheumatol Phys. Med. 11(5):217-224 (1972).
Kates, et al., "Experiences of Arthroplasty of the Rheumatoid Knee Using MacIntosh Prostheses," Ann. Rheum. Dis. 28(3):328 (1969).
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Kim et al., "Measurement of Femoral Neck Anteversion in 3D. Part 1: 3D Imaging Method," Med. and Viol. Eng. and Computing, vol. 38, No. 6, pp. 603-609, 2000.
Kshirsagar et al., "Measurement of Localized Cartilage Volume and Thickness of Human Knee Joints by Computer Analysis of Three-Dimensional Magnetic Resonance Images", Invest Radiol. May 1998, 33(5): 289-299 T. 111, V. 111.
Lam et al., "X-Ray Diagnosis: A Physician's Approach", Editor Lam, 1998, Springer-Verlag publishers, Title page and Table of Contents pgs. Only (ISBN 9813083247).
Lam et al., "Varus/Valgus Alignment of the Femoral Component in Total Knee Arthroplasty," The Knee, vol. 10, pp. 237-241, 2003.
Leenslag et al., "A Porous Composite for Reconstruction of Meniscus Lesions," Biological and Biomechanical Perform. of Biomaterials, Elsevier Science Publishers Amsterdam pp. 147-152 (1986).
Lu et al., "In vitro degradation of porous poly(L-lactic acid) foams", Biomaterials, 21(15):1595-1605, Aug. 2000.
MacIntosh, "Arthroplasty of the Knee in Rheumatoid Arthritis," Proceedings and Reports of Councils and Assotions, J. Bone & Joint Surg., vol. 48B No. (1):179 (Feb. 1996).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Mahaisavariya et al., "Morphological Study of the Proximal Femur: A New Method of Geometrical Assessment Using 3 Dimensional Reverse Engineering," Med. Eng. and Phys., vol. 24, pp. 617-622, 2002.
Marler et al., "Soft-Tissue Augmentation with Injectable Alginate and Syngeneic Fibroblasts", Plastic & Reconstructive Surgery, 105(6):2049-2058, May 2000.
Matsen, III et al., "Robotic Assistance in Orthopaedic Surgery: A Proof of Principle Using Distal Femoral Arthroplasty", Clinical Ortho. and Related Research, 296:178-186 (1993).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).

(56) References Cited

OTHER PUBLICATIONS

Nelson et al., "Arthroplasty and Arthrodesis of the Knee Joint," Orthop. Clin. North Am. 2 (1): 245-64 (1971).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Ranawat et al., "MacIntosh Hemiarthroplasty in Rheumatoid Knee," Acta Orthop Belg., 39 (1): 1-11 (1973).
Schorn et al., "MacIntosh Arthroplasty in Rheumatoid Arthritis," Rheumatol Rehabil. Aug. 1978:17(3):155-163.
Slone et al., "Body CT: A Practical Approach", Editor Slone, 1999 McGraw-Hill publishers, Title page and Table of Contents pgs. Only (ISBN 007058219).
Stauffer et al., "The MacIntosh Prosthesis. Prospective Clinical and Gait Evaluation," Arch. Surg. 110(6):717-720 (1975).
Stout et al., "X-Ray Structure Determination: A Practical Guide", 2nd Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Testi et al., "Border Tracing Algorithm Implementation for the Femoral Geometry Reconstruction," Comp. Meth. and Programs in Biomed., vol. 65, pp. 175-182, 2001.
Vandeberg et al., "Assessment of Knee Cartilage in Cadavers With Dual-Detector Spiral CT Arthrography and MR Imaging", Radiology, Feb. 2002: 222(2): 430-435.
Wiese et al., "Biomaterial properties and biocompatibility in cell culture of a novel self-inflating hydrogel tissue expander", J. Biomedical Materials Research Part A, 54(2):179-188, Nov. 2000.
Wordsworth et al., "MacIntosh Arthroplasty for the Rheumatoid Knee: A 10-year Follow Up," Ann. Rheum. Dis. 44(11):738-741 (1985).
Yusof et al., "Preparation and characterization of chitin beads as a wound dressing precursor", J. Biomedical Materials Research Part A, 54(1):59-68, Oct. 2000.
International Searching Authority, International Search Report—International Application No. PCT/US04/39616, dated Mar. 28, 2005, together with the Written Opinion of the International Searching Authority, 6 pages.
International Searching Authority, International Search Report—International Application No. PCT/US2006/045172, dated Apr. 19, 2007, 5 pages.
European Patent Office, Supplementary European Search Report—Application No. 04812187.5, dated Sep. 27, 2007, 3 pages.
International Searching Authority, International Search Report—International Application No. PCT/US2008/066994, dated Feb. 19, 2009, together with the Written Opinion of the International Searching Authority, 16 pages.
Bromberg & Sunstein LLP, Amendment dated Sep. 22, 2008, pertaining to U.S. Appl. No. 09/882,363, 15 pages.
United States Patent and Trademark Office, Office Action dated Jan. 6, 2009, pertaining to U.S. Appl. No. 09/882,363, 9 pages.
Bromberg & Sunstein LLP, Request for Continued Examination dated Jul. 6, 2009, pertaining to U.S. Appl. No. 09/882,363, 16 pages.
International Searching Authority, International Search Report—International Application No. PCT/US2009/036189, dated Jul. 13, 2009, together with the Written Opinion of the International Searching Authority, 11 pages.
Sunstein Kann Murphy & Timbers LLP, Supplemental Amendment dated Sep. 18, 2009, pertaining to U.S. Appl. No. 09/882,363, 11 pages.
United States Patent and Trademark Office, Office Action dated May 5, 2008, pertaining to U.S. Appl. No. 10/724,010, 13 pages.
Bromberg & Sunstein LLP, Request for Continued Examination and Response dated Nov. 4, 2008, pertaining to U.S. Appl. No. 10/724,010, 15 pages.
United States Patent and Trademark Office, Office Action dated Jan. 29, 2009, pertaining to U.S. Appl. No. 10/724,010, 9 pages.
Bromberg & Sunstein LLP, Response to Office Action dated Jan. 29, 2009, pertaining to U.S. Appl. No. 10/724,010, 16 pages.
United States Patent and Trademark Office, Office Action dated Nov. 26, 2007, pertaining to U.S. Appl. No. 11/002,573, 15 pages.
Bromberg & Sunstein LLP, Request for Continued Examination and Response dated Feb. 27, 2008, pertaining to U.S. Appl. No. 11/002,573, 19 pages.
United States Patent and Trademark Office, Office Action dated May 9, 2008, pertaining to U.S. Appl. No. 11/002,573, 17 pages.
Bromberg & Sunstein LLP, Amendment dated Aug. 12, 2008, pertaining to U.S. Appl. No. 11/002,573, 25 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.
Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
United States Patent and Trademark Office, Office action dated Jan. 26, 2010, pertaining to U.S. Appl. No. 11/671,745, 9 pages.
International Searching Authority, International Search Report—International Application No. PCT/US10/31415, dated Jun. 29, 2010, together with the Written Opinion of the International Searching Authority, 9 pages.
Portheine et al., In German: "Computer-Assisted Total Knee Endoprosthetics with Planning-Specific Treatement Templates", Biomed. Tech., vol. 46, Supp. vol. 1, Jan. 2001.
Portheine et al., English Translation with Certification: "Computer-Assisted Total Knee Endoprosthetics with Planning-Specific Treatement Templates", Biomed. Tech., vol. 46, Supp. vol. 1, Jan. 2001.
European Patent Office, Extended European Search Report—Application No. 10765271.1-2310, dated Dec. 19, 2012, 6 pages.
European Patent Office, European Search Report—Application No. 12170854.9-1526 dated Oct. 9, 2012, 6 pages.
Macdonald et al., "Inaccuracy of Acetabular Reaming Under Surgical Conditions", Journ. of Arthro., vol. 14, No. 6, pp. 730-737, 1999.
Müller-Wittig et al., "A Computer-Assisted Planning System for Total Knee Replacement", CG Topics, pp. 17-19, Jun. 2000.
International Searching Authority, International Search Report—International Application No. PCT/US2013/025216 dated May 30, 2013, 5 pages.
European Patent Office, Extended European Search Report—Application No. 13164557.4-1659 dated Nov. 25, 2013, 8 pages.
European Patent Office, Extended European Search Report—Application No. 13167237.0-1659 dated Nov. 25, 2013, 8 pages.
European Patent Office, Extended European Search Report—Application No. 13167246.1-1659 dated Nov. 25, 2013, 8 pages.
European Patent Office, Extended European Search Report—Application No. 13167257.8-1659 dated Nov. 25, 2013, 8 pages.

(56) References Cited

OTHER PUBLICATIONS

United States Patent and Trademark Office, Office Action pertaining to U.S. Appl. No. 13/405,843 dated Dec. 10, 2013, 9 pages.

United States Patent and Trademark Office, Office Action dated Feb. 13, 2014, pertaining to U.S. Appl. No. 13/306,501, 25 pages.

Cohen et al., "Computer-Aided Planning of Patellofemoral Joint OA Surgery: Developing Physical Models from Patient MRI", MICCAI, Oct. 11-13, 1998, 13 pages.

Cohen et al., "Knee Cartilage Topography Thickness and Contact Areas From MRI: In-Vitro Calibration and In-Vivo Measurements", Osteoarthritis and Cartilage vol. 7, No. 1, pp. 95-109 (1999).

Tsai et al., "Accurate Surface Voxelization for Manipulating Volumetric Surfaces and Solids with Application in Simulating Musculoskeletal Surgery", Inst. of Information and Computer Engineering, pp. 234-243, 2001.

International Searching Authority, International Search Report—International Application No. PCT/US2012/025269 dated Aug. 31, 2012, together with the Written Opinion of the International Searching Authority, 14 pages.

International Searching Authority, International Search Report—International Application No. PCT/US2012/025274 dated Oct. 25, 2012, together with the Written Opinion of the International Searching Authority, 12 pages.

International Searching Authority, International Search Report—International Application No. PCT/US2012/025277 dated Oct. 25, 2012, together with the Written Opinion of the International Searching Authority, 12 pages.

International Searching Authority, International Search Report—International Application No. PCT/US2012/025280 dated Oct. 25, 2012, together with the Written Opinion of the International Searching Authority, 11 pages.

United States Patent and Trademark Office Office Action dated Jul. 28, 2014 pertaining to U.S. Appl. No. 13/305,635, 12 pages.

\* cited by examiner

SURGICAL CUTTING GUIDE

CROSS REFERENCE TO RELATED APPLICATIONS

The present application claims the benefit of U.S. application Ser. No. 60/943,726, entitled "SURGICAL CUTTING GUIDE" filed Jun. 13, 2007, which application is incorporated herein by reference in its entirety.

TECHNICAL FIELD

The present invention relates to surgical tools, and more particularly, to surgical tools such as surgical cutting guides.

BACKGROUND ART

When performing cuts with blades, saws, or other surgical instruments during surgical interventions, surgeons typically have good control of the surgical instrument with regard to direction and depth of tissue penetration. However, sometimes a surgical instrument may slip, be deflected, or stray from its intended cutting path. When a surgical instrument strays from its indented cutting path, it may inadvertently injure or cut other tissues.

For example, in knee arthroplasty, a surgeon may intend to preserve one or more tibial spines. When performing a horizontal tibial cut, the surgeon typically guides the blade in an anteroposterior direction. The surgeon guides the blade path so as to stay clear of the tibial spines. However, if the surgeon accidentally misdirects the instrument or if the instrument is deflected from its intended path, the blade path may extend into the tibial spines or other local tissues. This unintended cut of the tibial spines may result in the loss of ligament stability.

Deviation of the surgical instrument from its intended cutting path may also have harmful effects when performing surgical interventions in other parts of the body. For example, in the spine, deviation of a surgical instrument may result in neural damage or damage to bony or disc structures. In the hip, deviation of an instrument from the cutting path may potentially result in neurovascular damage or damage to bony and ligamentous structures. In a shoulder, deviation of the instrument path may potentially result in neurovascular or muscular damage.

Deviation from the cutting path may also lead to other unintended consequences. For example, failure to follow a cutting path may later result in misalignment or poor positioning of an implant. A poor fit for an implant may result in complete failure of the implant or other complications.

SUMMARY OF THE INVENTION

Embodiments of the present invention are directed to preventing unintended and inadvertent cuts to tissues during surgical interventions. In one embodiment of the invention, a surgical cutting guide is used to prevent unintended and inadvertent cuts. The surgical cutting guide includes a contact surface that conforms to a surface associated with a biological tissue and at least one guide for restricting movement of a surgical instrument in a first direction and for allowing the movement of the surgical instrument in a second direction along a cutting path across the surface of the tissue. The guide further includes a stop for restricting movement of the surgical instrument in the second direction along the cutting path. The stop is based at least, in part, on patient specific information.

In some embodiments, the guide may be configured to abut the tissue and the abutment of the guide and tissue defines at least part of the cutting path of the surgical instrument. The stop may also be configured to abut the tissue.

Each of the stop, the guide, and the contact surface may have several configurations. For example, the stop may be configured to contact a cutting surface of the surgical instrument. The surgical instrument may be a blade or a saw. The stop may also be perpendicular to a cut plane defined by the guide. The guide may be one of a slot, an aperture, and a cutting plane. The placement, location, orientation, and shape of the stop may be based at least, in part, on patient specific information. The contact surface may be a mirror image of an uncut surface of the tissue. Also, the contact surface may have a plurality of concavities and/or a plurality of convexities. The contact surface may also be based at least, in part, on patient specific information. The contact surface may be made to conform to a variety of tissues, for example, the tissue may be one of a joint, an articular surface, a spine, a structure adjacent to one of a joint, an articular surface, and a spine.

In some exemplary embodiments of the invention, the patient specific information may be based on an image of the tissue. The images may be one of a CT image, a spiral CT image, an MRI image, an ultrasound image, a digital tomosynthesis image, and an optical coherence tomograph. In other embodiments, the patient specific information is based at least, in part, on intra-operative measurement of the tissue.

In some embodiments of the present invention, the stop may protect the tibial spines. In a more particular embodiment, the guide guides movement of the surgical instrument towards the tibial spines and the stop prevents the surgical instrument from cutting the tibial spines. In other embodiments, the stop protects one of a ligament, a vessel, a nerve, a muscle, a bony structure, and a cartilaginous structure. Further embodiments of the present invention may be put to use in one of a knee, a hip, an ankle, a foot. a shoulder, an elbow, a wrist, a hand, a spine, a vertebral endplate, a skull, a pedicle, a posterior element, and a spinous process.

In another embodiment of the present invention, the surgical cutting guide includes a surface that is a mirror image of a joint, a spine, or a structure adjacent to a joint or spine. The surgical cutting guide further includes a guide or a guide aperture that directs movement of a surgical instrument along a predetermined path. A stop prevents the surgical instrument from deviating from the predetermined path. The location of said stop may be based, at least in part, on patient specific information.

In further related embodiments of the invention, the stop may protect one or more tibial spines. The guide or guide aperture may direct movement of the surgical instrument towards the tibial spine, wherein the stop keeps the surgical instrument clear of the tibial spine. The guide or guide aperture may direct movement of a saw and/or blade. The surgical cutting guide may be used in a knee, a hip, an ankle, a foot, a shoulder, an elbow, a wrist, a hand, a spine, a vertebral endplate, a skull, a pedicle, a posterior element, or a spinous process. The surface may have a plurality of concavities and/or a plurality of convexities. The stop may be perpendicular to a cut plane defined by the at least one of a guide and a guide aperture.

In accordance with another embodiment of the invention, a surgical tool for a knee joint includes a portion that is a mirror image of a joint, a spine, and/or a structure adjacent to a joint or a spine. The surgical tool further includes a guide or a guide aperture that directs movement of a surgical instrument along a predetermined path. A stop inhibits the surgical instrument from deviating from the predetermined path, wherein said stop protects a tibial spine.

In accordance with related embodiments of the invention, the surgical tool may be used for a total knee arthroplasty or a partial knee arthroplasty. The position of the stop may be based, at least in part, on patient specific information. The guide or guide aperture may direct movement of the surgical instrument towards the tibial spine, wherein the stop keeps the surgical instrument clear of the tibial spine. The guide or guide aperture may direct movement of a saw and/or blade. The surface may have a plurality of concavities and/or a plurality of convexities. The stop may be perpendicular to a cut plane defined by the at least one of a guide and a guide aperture.

In accordance with another embodiment of the invention, a cutting guide includes a portion that is a mirror image of a joint, a spine, and/or a structure adjacent to a joint or a spine. The cutting guide further includes a guide or a guide aperture for directing movement of a surgical instrument along a predetermined path. A stop prevents a surgical instrument from deviating from the predetermined path, where the stop may protect a ligament, a vessel, a nerve, a muscle, a bony structure, and/or a cartilaginous structure.

In accordance with related embodiments of the invention, the surgical tool may be used in a total knee arthroplasty or a partial knee arthroplasty. The position of the stop may be based, at least in part, on patient specific information. The guide and/or guide aperture may direct movement of the surgical instrument towards the ligament, vessel, nerve, muscle, bony structure, and/or cartilaginous structure, but the stop may keep the surgical instrument clear of the ligament, vessel, nerve, muscle, bony structure, and/or cartilaginous structure. The guide or guide aperture may direct movement of one of a saw and a blade. The portion may be a surface having a plurality of concavities and a plurality of convexities. The stop may be perpendicular to a cut plane defined by the at least one of a guide and a guide aperture.

In accordance with another embodiment of the invention, a cutting guide includes a portion that is a mirror image of a joint, a spine, and/or a structure adjacent to the joint or spine. The cutting guide further includes a guide or a guide aperture that directs movement of a surgical instrument along a predetermined path. A stop inhibits the surgical instrument from deviating from the predetermined path. The stop is integrated into said cutting guide.

In accordance with related embodiments of the invention, the position of the stop is based, at least in part, on patient specific information. The stop may protect the tibial spines. The guide or guide aperture may direct movement of the surgical instrument towards the tibial spines, wherein the stop keeps the surgical instrument clear of the tibial spines. The guide or guide aperture may direct movement of a saw and/or blade. The surgical cutting guide may be used in a knee, a hip, an ankle, a foot, a shoulder, an elbow, a wrist, a hand, a spine, a vertebral endplate, a skull, a pedicle, a posterior element, or a spinous process. The surface may have a plurality of concavities and/or a plurality of convexities. The stop may be perpendicular to a cut plane defined by the at least one of a guide and a guide aperture.

In accordance with another embodiment of the invention, a cutting guide includes a portion that is a mirror image of a joint, a spine, and/or a structure adjacent to the joint or spine. The cutting guide further includes a guide or guide aperture that directs movement of a surgical instrument along a predetermined path. A stop inhibits the surgical instrument from deviating from the predetermined path. The stop is attached to said cutting guide.

In accordance with related embodiments of the invention, the position of the stop is based, at least in part, on patient specific information. The stop may protect the tibial spine. The guide or guide aperture may direct movement of the surgical instrument towards the tibial spine, wherein the stop keeps the surgical instrument clear of the tibial spine. The guide or guide aperture may direct movement of a saw and/or blade. The surgical cutting guide may be used in a knee, a hip, an ankle, a foot, a shoulder, an elbow, a wrist, a hand, a spine, a vertebral endplate, a skull, a pedicle, a posterior element, or a spinous process. The surface may have a plurality of concavities and/or a plurality of convexities. The attachment may be via a block or a linkage. The stop may be perpendicular to a cut plane defined by the at least one of a guide and a guide aperture.

In accordance with another embodiment of the invention, a cutting guide includes a portion that is a mirror image of a joint, a spine, and/or a structure adjacent to the joint or spine. The cutting guide further includes a guide or a guide aperture that directs movement of a surgical instrument along a predetermined path. A stop inhibits the surgical instrument from deviating from the predetermined path. The position, orientation or shape of the stop is derived using patient specific anatomic information.

In accordance with related embodiments of the invention, the position, orientation, or shape of said stop may allow for intra-operative adjustments. The stop may protect the tibial spine. The guide or guide aperture may direct movement of the surgical instrument towards the tibial spine, wherein the stop keeps the surgical instrument clear of the tibial spine. The guide or guide aperture may direct movement of a saw and/or blade. The cutting guide may be used in a knee, a hip, an ankle, a foot, a shoulder, an elbow, a wrist, a hand, a spine, a vertebral endplate, a skull, a pedicle, a posterior element, or a spinous process. The surface may have a plurality of concavities and/or a plurality of convexities. The stop may be perpendicular to a cut plane defined by the at least one of a guide and a guide aperture.

In accordance with another embodiment of the invention, a surgical cutting guide includes a surface that is a mirror image of at least one of a joint, a spine, and a structure adjacent to one of a joint and a spine. The surgical cutting guide further includes at least one of a guide and a guide aperture for directing movement of a surgical instrument along a predetermined path. The position or shape or orientation of the at least one of a guide and a guide aperture is based on patient specific information and provides for at least one of a predetermined cut angulation and a predetermined cut height.

In accordance with related embodiments of the invention, the surgical tool may further include a stop for inhibiting the surgical instrument from deviating from the predetermined path. The position of the stop may be based, at least in part, on patient specific information. The stop may protect the tibial spine. At least one of a guide and a guide aperture may direct movement of the surgical instrument towards the tibial spine, but the stop may keep the surgical instrument clear of the tibial spine. The at least one of a guide and a guide aperture may be used to direct movement of a saw or a blade with regard to, for example, a knee, a hip, an ankle, a foot, a shoulder, an elbow, a wrist, a hand, a spine, a vertebral endplate, a skull, a pedicle, a posterior element, or a spinous process.

In accordance with related embodiments of the above-described embodiments of the invention, the patient specific information may be based, at least in part, on an intra-operative measurement of the joint, the spine, or the structure adjacent to the joint and the spine. Alternatively, or in combination with the intra-operative measurement, the patient specific information may be based on an image of the joint, the spine, or the structure adjacent to the joint and the spine. The image may be a CT image, a spiral CT image, an MRI image, an ultrasound image, a digital tomosynthesis image, and an optical coherence tomograph.

In accordance with another embodiment of the invention, a surgical tool includes a template having at least one a guide for directing movement of a surgical instrument along a predetermined path. At least one insert is attached to the guide or guide aperture. The at least one insert protects the template from the surgical instrument.

In accordance with related embodiments of the invention, the template may be made of plastic, and the insert is made of metal. The template may be a mold or a rapid prototype. The insert may be removably attached to the template. The insert may snap onto the template.

Embodiments of the present invention are also directed to a method for guiding a surgical instrument. The method includes providing a surgical cutting guide having a contact surface that conforms to a surface associated with a biological tissue and at least one guide for restricting movement of a surgical instrument in a first direction and for allowing the movement of the surgical instrument in a second direction along the cutting path across the surface of the tissue. Providing the surgical guide further includes ascertaining patient specific information associated with the tissue and incorporating a stop into the guide for restricting movement of the surgical instrument in the second direction along the cutting path. The stop is based at least, in part, on patient specific information.

The method may further include securing the cutting guide to the tissue and cutting the tissue by using the cutting guide to guide the surgical instrument along the cutting path. The cutting guide may be secured to the guide by using anchor screws. In one embodiment of the method, the tissue may be cut so that a cutting surface of the surgical instrument contacts the stop. A blade and/or a saw may be used to cut the tissue.

The method may include several configurations of the surgical cutting guide. For example, the guide and/or the stop may be configured to abut the surface of the tissue. The guide may also be configured into a slot, an aperture, and/or a cutting plane. The placement, location, orientation, and shape of the stop may be based at least, in part, on patient specific information. For example, in one embodiment the stop may be configured to be perpendicular to a cut plane defined by the guide.

The contact surface may be configured so that at least a portion of the contact surface is a mirror image of an uncut surface of the tissue. The contact surface may also be based at least, in part, on patient specific information. The contact surface may further include a plurality of concavities and a plurality of convexities.

In some embodiments of the method, the patient specific information may be ascertained through imaging the tissue. Imaging may be accomplished by CT imaging, CT spiral imaging, MRI imaging, ultrasound imaging, digital tomosynthesis, and/or optical coherence tomography. In other embodiments of the method, patient specific information may be ascertained through intra-operative measuring.

Embodiments of the method may be applied to a variety of tissues, for example, the tissue may be one of a joint, an articular surface, a spine, and a structure adjacent to one of a joint, an articular surface, and a spine. Embodiments of the method may also be put to use in one of a knee, a hip, an ankle, a foot, a shoulder, an elbow, a wrist, a hand, a spine, a vertebral endplate, a skull, a pedicle, a posterior element, and a spinous process.

In another embodiment of the surgical cutting guide, the cutting guide includes a contact surface that conforms to a surface associated with the tissue and at least one guide for restricting movement of a surgical instrument in a first direction and for allowing the movement of the surgical instrument in a fifth direction along a cutting path into the tissue. The cutting guide further includes a stop for restricting movement of the surgical instrument in a second direction. The stop is based at least, in part, on patient specific information. In some embodiments, this guide may be configured to abut the tissue and the abutment of the guide and tissue defines at least part of the cutting path of the surgical instrument. The stop may also be configured to abut the tissue.

Each of the stop, the guide, and the contact surface may have several configurations. For example, the stop may be configured to contact a cutting surface of the surgical instrument. The surgical instrument may be a blade or a saw. The stop may also be perpendicular to a cut plane defined by the guide. The guide may be one of a slot, an aperture, and a cutting plane. The placement, location, orientation, and shape of the stop may be based at least, in part, on patient specific information. The contact surface may be a mirror image of an uncut surface of the tissue. Also, the contact surface may have a plurality of concavities and/or a plurality of convexities. The contact surface may also be based at least, in part, on patient specific information. The contact surface may be made to conform to a variety of tissues, for example, the tissue may be one of a joint, an articular surface, a spine, a structure adjacent to one of a joint, an articular surface, and a spine.

In some exemplary embodiments of the invention, the patient specific information may be based on an image of the tissue. The images may be one of a CT image, a spiral CT image, an MRI image, an ultrasound image, a digital tomosynthesis image, and an optical coherence tomograph. In other embodiments, the patient specific information is based at least, in part, on intra-operative measurement of the tissue.

In some embodiments of the present invention, the stop may protect the tibial spines. In a more particular embodiment, the guide guides movement of the surgical instrument towards the tibial spines and the stop prevents the surgical instrument from cutting the tibial spines. In other embodiments, the stop protects one of a ligament, a vessel, a nerve, a muscle, a bony structure, and a cartilaginous structure. Further embodiments of the present invention may be put to use in one of a knee, a hip, an ankle, a foot. a shoulder, an elbow, a wrist, a hand, a spine, a vertebral endplate, a skull, a pedicle, a posterior element, and a spinous process.

In another embodiment of the method for guiding a surgical instrument, the method includes providing a surgical cutting guide having a contact surface that conforms to a surface associated with a tissue and at least one guide for restricting movement of a surgical instrument in a first direction and for allowing the movement of the surgical instrument in a fifth direction along the cutting path into the tissue. Providing the surgical guide further includes ascertaining patient specific information associated with the tissue and incorporating a stop into the guide for restricting movement of the surgical instrument in the second direction. The stop is based at least, in part, on patient specific information. The method may further include securing the cutting guide to the tissue and cutting the tissue by using the cutting guide to guide the surgical instrument along the cutting path. The cutting guide may be secured to the guide by using anchor screws. In one embodiment of the method, the tissue may be cut so that a cutting surface of the surgical instrument contacts the stop. A blade and/or a saw may be used to cut the tissue.

The method may include several configurations of the surgical cutting guide. For example, the guide and/or the stop may be configured to abut the surface of the tissue. The guide may also be configured into a slot, an aperture, and/or a cutting plane. The placement, location, orientation, and shape of the stop may be based at least, in part, on patient specific information. For example, in one embodiment the stop may be configured to be perpendicular to a cut plane defined by the guide.

The contact surface may be configured so that at least a portion of the contact surface is a mirror image of an uncut surface of the tissue. The contact surface may also be based at least, in part, on patient specific information. The contact surface may further include a plurality of concavities and a plurality of convexities.

In some embodiments of the method, the patient specific information may be ascertained through imaging the tissue. Imaging may be accomplished by CT imaging, CT spiral imaging, MRI imaging, ultrasound imaging, digital tomosynthesis, and/or optical coherence tomography. In other embodiments of the method, patient specific information may be ascertained through intra-operative measuring.

Embodiments of the method may be applied to a variety of tissues, for example, the tissue may be one of a joint, an articular surface, a spine, and a structure adjacent to one of a joint, an articular surface, and a spine. Embodiments of the method may also be put to use in one of a knee, a hip, an ankle, a foot, a shoulder, an elbow, a wrist, a hand, a spine, a vertebral endplate, a skull, a pedicle, a posterior element, and a spinous process.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
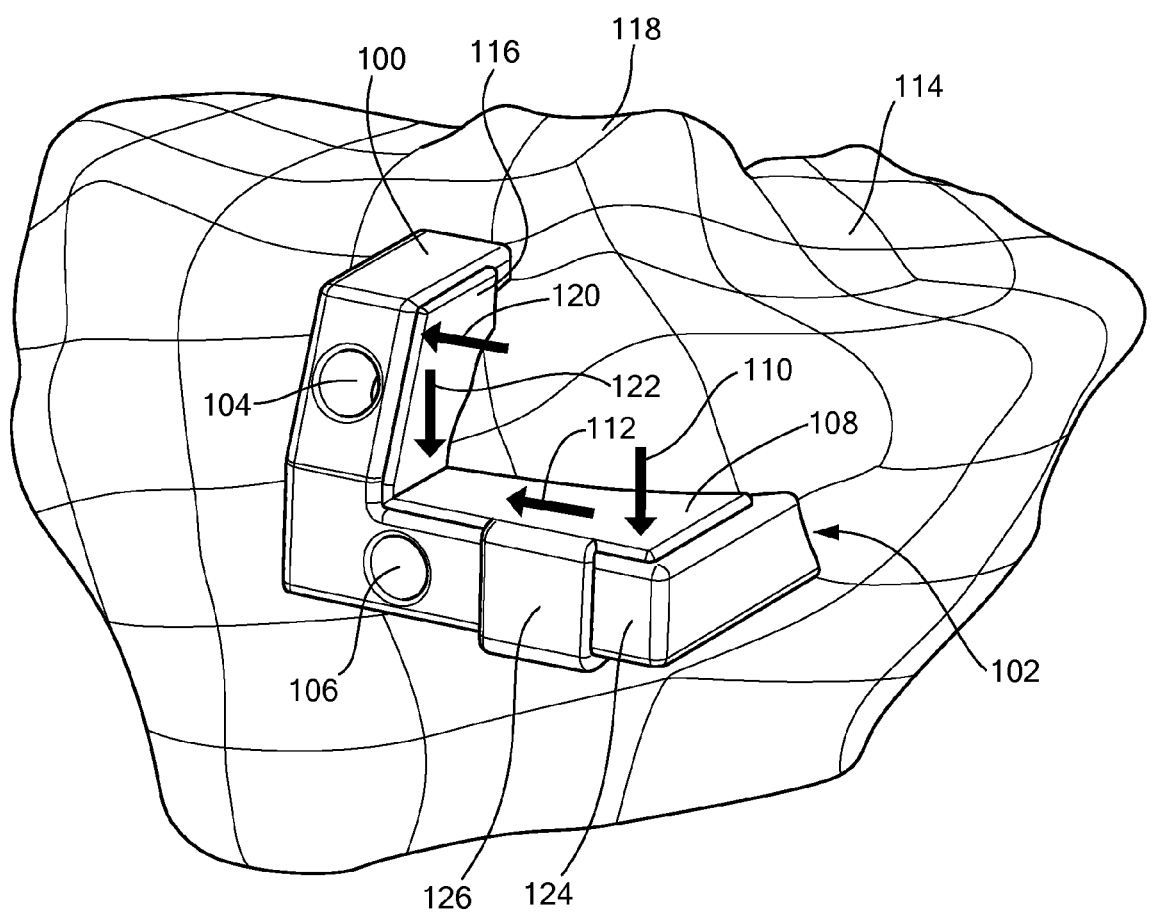
FIG. 1 is an isometric view of a patient specific surgical tool, in accordance with one embodiment of the invention.

Illustrative embodiments of the present invention are directed to a patient specific surgical cutting guide. FIG. 1 is an isometric view of a patient specific surgical cutting guide 100, in accordance with one embodiment of the invention. More particularly, the exemplary surgical cutting guide 100 shown in FIG. 1 is a patient specific cutting guide (also referred to in the art as a jig or template) that may be used, for example, in performing a knee arthroplasty. In other embodiments, the surgical guide 100 may be used in performing operations elsewhere in the body, such as a joint, a hip, an ankle, a foot, a shoulder, an elbow, a wrist, a hand, a spine, a vertebral endplate, a skull, a pedicle, a posterior element, and/or a spinous process.

The surgical cutting guide 100 includes a contact surface 102 that conforms to at least a portion of a surface of a biological tissue to be treated or the structures adjacent to the tissue, as described in U.S. application Ser. No. 11/671,745, incorporated herein by reference in its entirety. In preferred embodiments, the contact surface 102 conforms to a substantially uncut portion of a surface of a biological tissue to be treated or the structures adjacent to the tissue. When in use, the contact surface 102 of the cutting guide 100 is placed in contact with the tissue and/or structures adjacent to the tissue. The conforming structure of the contact surface 102 helps ensure proper positioning and orientation of the cutting guide 100. The contact surface 102 may be used to contact a variety of different tissues. For example, the tissue may be, without limitation, at least one of an articular surface, cartilage, subchondral bone and/or other tissue surface and shape. In some embodiments the contact surface 102 may be a "mirror image" or "negative" of the surface of the tissue. Yet, in other embodiments, the contact surface 102 may only have portions that conform to the surface of the tissue. The contact surface 102 may be, without limitation, a surface with one or more concavities and/or one or more convexities. For example, the contact surface 102 may have, without limitation, a single convexity; a plurality of convexities; a single concavity; a plurality of concavities; or at least one convexity and at least one concavity.

In order to fix the contact surface 102 to the tissue, the surgical cutting guide 100 may contain drill bushing holes 104 and 106. These drill bushing holes 104, 106 allow the cutting guide 100 to be anchored to the tissue and/or adjacent structures by using anchoring screws or drill pins inserted through the drill bushing holes 104, 106. In various embodiments, the drill bushing holes 104, 106 include metal inserts (or other hard material) to prevent degradation of the cutting guide when drilling. Other attachment mechanisms known in the art may be used to fix the contact surface 102 to the tissue.

Patient specific information may advantageously be used to ensure that the contact surface 102 properly conforms to the surface of the tissue. Patient specific information includes, but is not limited to one or more intra-operative measurements and/or one or more electronic images. Images and measurements of the surface of the tissue provide object coordinates that define the surface and shape of the tissue. The electronic images of the tissue may be from, without limitation, a CT image, a spiral CT image, an MRI image, an ultrasound scan, digital tomosynthesis, or optical coherence tomography. The object coordinates may be utilized to shape a portion of the cutting guide 100. For example, once the patient specific information is ascertained, rapid prototyping or other manufacturing techniques may be used to adapt the contact surface 102 to the patient's particular tissue structure. In various embodiments, a mold may be made to form the contact surface 102 to the particular tissue structure of the patient. Alternatively, the patient specific information may be used to select a pre-made guide or template that has a good fit with a patient's particular tissue structure.

The surgical cutting guide 100 includes at least one guide 108 for restricting movement of the surgical instrument in a first direction 110 and allowing movement of the surgical instrument in a second direction 112 along a cutting path across the surface of the tissue. The guide 108 defines at least a portion of the cutting path of the surgical instrument along the surface of the tissue. The cutting path may be predetermined based upon the patient specific information and the type of surgical intervention being performed. In one embodiment, as depicted in FIG. 1, the guide 108 is a simple cutting plane. But the guide 108 may also be formed from one or more cutting planes, apertures, slots, and/or holes to accommodate surgical instruments such as drills, reamers, curettes, k-wires, screws and saws. Moreover, a single cutting guide 100 may include a plurality of guides 108. The guide 108 or plurality of guides 108 may be positioned and/or adjusted based on the patient specific information to form a predetermined instrument cutting path for a desired surgical intervention.

Figure 2:
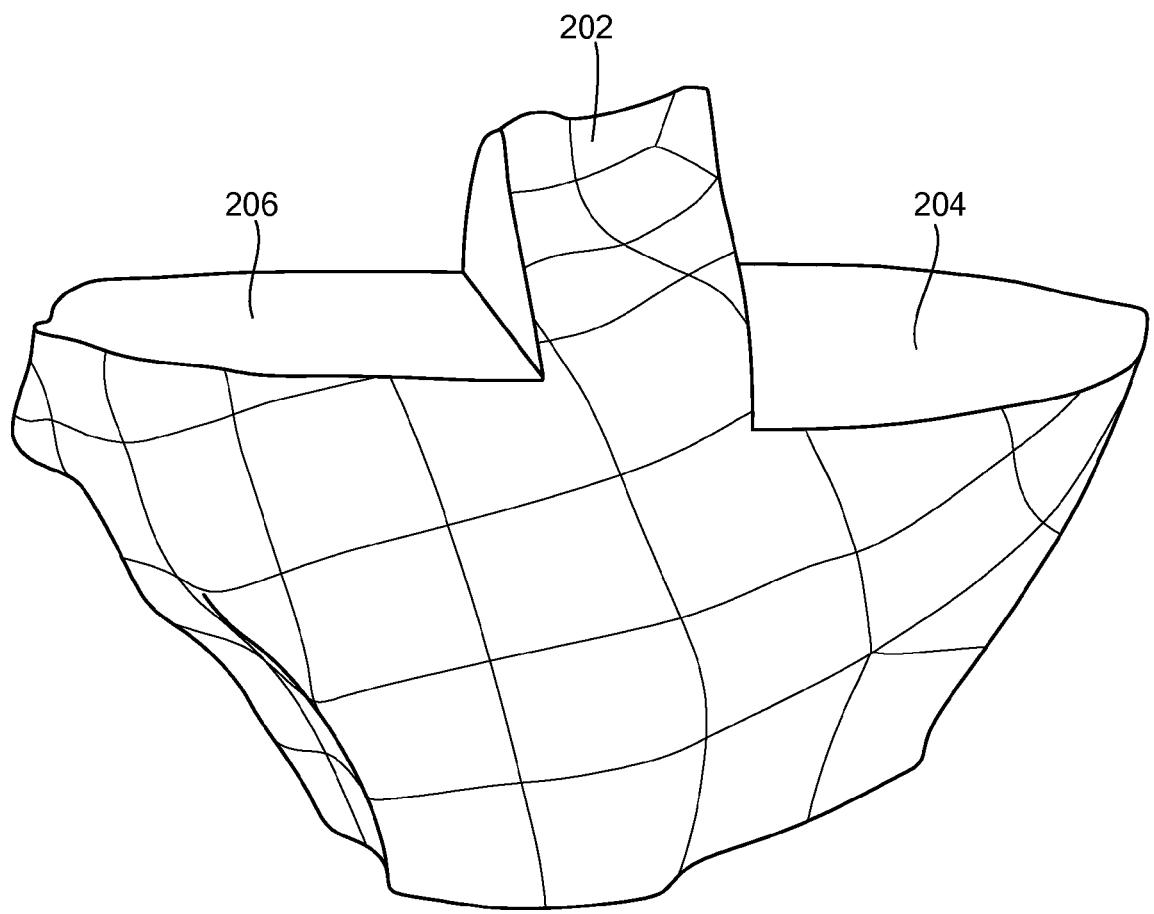
FIG. 2 depicts exemplary medial and lateral cuts made to the tibial plateau while preserving the tibial spines, in accordance with one embodiment of the invention.
Figure 3:
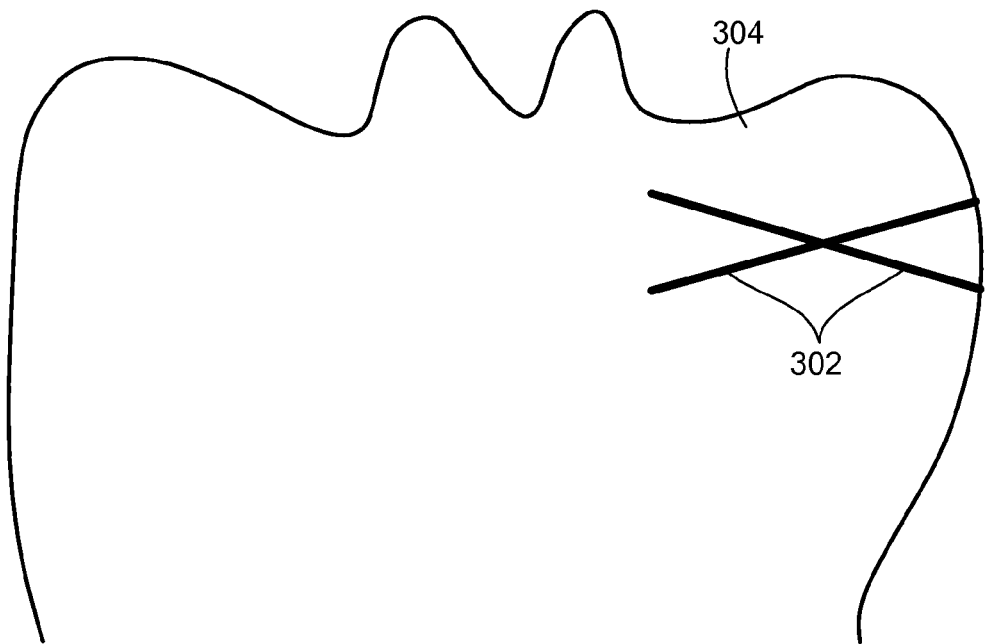
FIG. 3 depicts exemplary angular cuts on the tibial plateau.

During a knee arthroplasty, the guides 108 may direct horizontal medial 206 and lateral 204 cuts of the tibia plateau 114, as depicted (before and after) in FIG. 1 and FIG. 2. Yet, in another embodiment, the guides 108 may provide for angular cuts rather than horizontal or near horizontal cuts. FIG. 3 shows exemplary angular cuts 302 on the tibial plateau 304. The angulation of the cut may be, without limitation, anterior to posterior and/or lateral to medial. The position or placement of the horizontal or angular guide 108 on the surgical cutting guide 100 relative to the contact surface 102 may be patient specific, and, for example, may control, among other dimensions, the cut height on the tibial plateau.

As depicted in FIG. 1, the guide 108 may be configured to abut the surface of the tissue. In other words, at least a portion of an edge of the guide 108 may be in contact with the surface of the tissue. The abutment of the guide against the surface of the tissue may define a portion of the cutting path across the surface of the tissue. Yet, in other embodiments, the guide 108 may not be configured to contact the surface of the tissue and is, instead, set back from the surface of the tissue.

Figure 4:
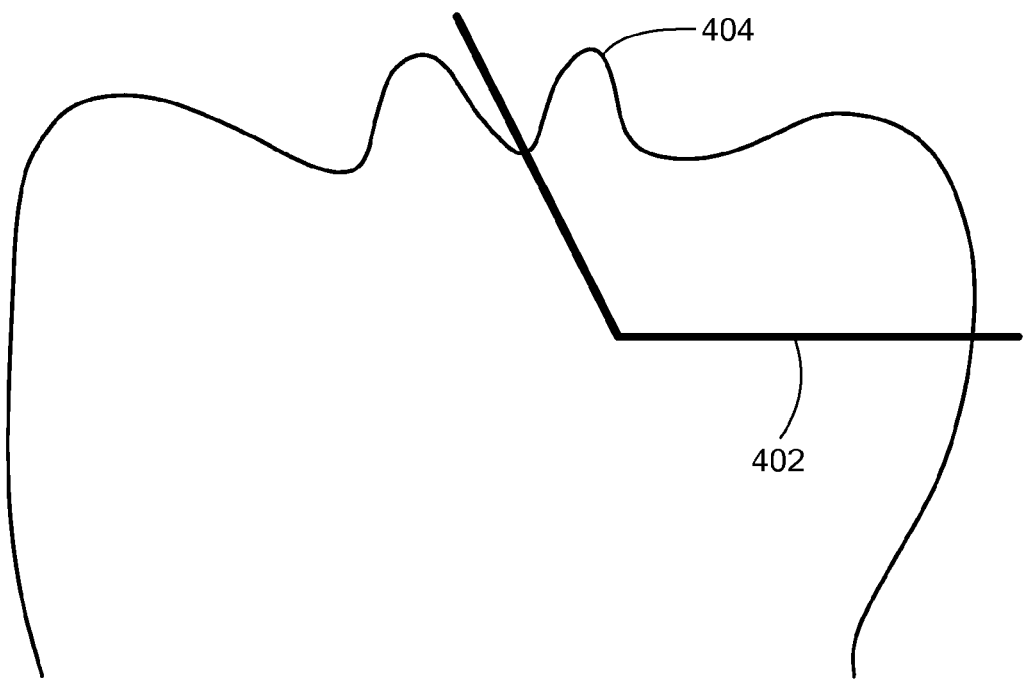
FIG. 4 depicts a tibial plateau with an exemplary cut plane that fails to preserve at least a portion of the tibial spines.

The cutting guide 100 also includes a stop 116 for restricting movement of the surgical instrument in the second direction along the cutting path. The stop 116 is used to prevent a surgical instrument from deviating from its intended path and ensures that the instrument will stay clear of tissue structures to be preserved. A single cutting guide may contain a plurality of stops 116. The stop 116 may be used to protect a variety of structures such as ligaments, vessels, nerves, muscles, bony structures, and cartilaginous structures. For example, in a knee arthroplasty, the patient specific surgical cutting guide 100 may include a guide 108 for directing a horizontal or near horizontal cut of the tibial plateau 114. In accordance with one aspect of the invention, FIG. 2 depicts exemplary medial 204 and lateral 206 cuts made to the tibial plateau 114 with properly preserved tibial spines 202. Whereas FIG. 4 depicts a tibial plateau showing a cut plane 402 that fails to preserve a portion of the tibial spines 404. In order to preserve the one or more tibial spines, the cutting guide 100 may include a medial stop 116 and/or a lateral stop 116. The stops 116 may be substantially perpendicular to the intended cutting plane defined by the guide 108 such as the stop 116 depicted in FIG. 1. In other embodiments, the stop 116 may be at other angles relative to the intended cutting plane, such as at 60, 70, or 80 degrees. Like the guide 108, the stop 116 may be configured to abut the surface of the tissue, or the stop 116 may be configured to be set back from the surface of the tissue. In various embodiments of the invention, the stop 116 may have a straight, curved, and/or complex surface. The stop 116 may have one or more convexities and/or concavities. Any shape known in the art is possible for the stop 116.

The cutting guide 100 also includes a stop 116 for restricting movement of the surgical instrument in the second direction along the cutting path. The stop 116 is used to prevent a surgical instrument from deviating from its intended path and ensures that the instrument will stay clear of tissue structures to be preserved. A single cutting guide may contain a plurality of stops 116. The stop 116 may be used to protect a variety of structures such as ligaments, vessels, nerves, muscles, bony structures, and cartilaginous structures. For example, in a knee arthroplasty, the patient specific surgical cutting guide 100 may include a guide 108 for directing a horizontal or near horizontal cut of the tibial plateau 114. In accordance with one aspect of the invention, FIG. 2 depicts exemplary medial 204 and lateral 206 cuts made to the tibial plateau 114 with properly preserved tibial spines 202. Whereas FIG. 4 depicts a tibial plateau showing a cut plane 402 that fails to preserve a portion of the tibial spines 404. In order to preserve the one or more tibial spines, the cutting guide 100 may include a medial stop 116 and/or a lateral stop 116. The stops 116 may be substantially perpendicular to the intended cutting plane defined by the guide 108 such as the stop 116 depicted in FIG. 1. In other embodiments, the stop 116 may be at other angles relative to the intended cutting plane, such as at 60, 70, or 80 degrees. Like the guide 108, the stop 116 may be configured to abut the surface of the tissue, or the stop 116 may be configured to be set back from the surface of the tissue. In various embodiments of the invention, the stop 116 may have a straight, curved, and/or complex surface. The stop 116 may have one or more convexities and/or concavities. Any shape known in the art is possible for the stop 116.

In another embodiment, as depicted in FIG. 1, the stop 116 may effectively be used as a guide by restricting the movement of the surgical tool in a third direction 120 and allowing the movement of the surgical instrument in a fourth direction 122 along the cutting path across the surface of the tissue. The guide 108 may effectively be used as a stop by restricting the movement of the surgical instrument in the fourth direction 122 along the cutting path.

In another embodiment of the present invention, an oscillating saw may be used to cut the tissue. In such an embodiment, the guide 108 of the surgical cutting guide 100 may restrict movement of the saw in a first direction 110 and may allow movement of the saw in a fifth direction into the tissue. A stop 116 may restrict movement of the saw in a second direction 112.

The placement, location, orientation, and shape of both the guide 108 and the stop 116 may be determined based on patient specific information. For example, patient specific information in the form of imaging data, which may be, without limitation, a CT image, a spiral CT image, an MRI image, an ultrasound scan, digital tomosynthesis, or optical coherence tomograph may be utilized to identify tissue structures that need to be preserved. The identification of tissue structures may be performed automatically or with the help of an operator. The guide 108 and the stop 116 may then be designed to ensure that the surgical instrument and its cutting path will stay clear of the tissue structure to be preserved. Intra-operative measurement of the tissue structure is another form of patient specific information that may be used to define the placement, location, orientation, and shape of the guide 108 and/or the stop 116.

Once the placement, location, orientation, and shape of the guide 108 and the stop 116 is determined, there are several ways to incorporate them into the cutting guide 100. In one embodiment the contact surface 102, the guide 108 and the stop 116 may be made of the same material. In such an embodiment, the contact surface 102, the guide 108, and the stop 116 may be molded or rapid prototyped as a single unitary structure. In another embodiment, the guide 108 and stop 116 may be integrated into the cutting guide 100. For example, the guide 108 and stop 116 may be machined into the cutting guide 100. However, in a preferred embodiment, the guide 108 and the stop 116 are made from hard materials, such as metal, in order to prevent the surgical instrument from penetrating and degrading the cutting guide 100. In such an embodiment, the guide 108 and stop 116 may be attached to the cutting guide 100 in an appropriate location and orientation. FIG. 1 depicts such an embodiment. The cutting guide 100 includes a template 124 that includes contact surface 102. The template 124 may be made from a material such as a plastic. The template 124 may be made from a mold or through rapid prototyping based on patient specific information. An insert 126 may be secured onto the template 124. As depicted in FIG. 1, the insert forms both the guide 108 and the stop 116. But in other embodiments separate inserts 126 may form each of the stop 116 and the guide 108. The insert 126 may be made from a hard material, such as metal, in order to protect the template 124 from the cutting surface of the surgical tool. The insert 126 may be removably attached to the template through the use of clips, pins, and/or anchor screws. In another embodiment, the guide 108 and stop 116 may be attached to the cutting guide 100 via a block or a linkage as described in U.S. application Ser. No. 11/671,745, incorporated herein by reference in its entirety.

In another embodiment, the guide 108 and/or stop 116 are incorporated into the cutting guide in such way that intra-operative adjustments may be made to the position, orientation and/or shape of the guide 108 or stop 116. A pivot, space, ratchet or jack like mechanism may be used, without limitation, to adjust the guide 108 or stop 116. For example, the stop 116 may be capable of sliding along the cutting guide 100 and, then, locking into place at the appropriate position. Such intra-operative adjustments may be performed, without limitation, to ensure optimal ligament balancing.

Figure 6:
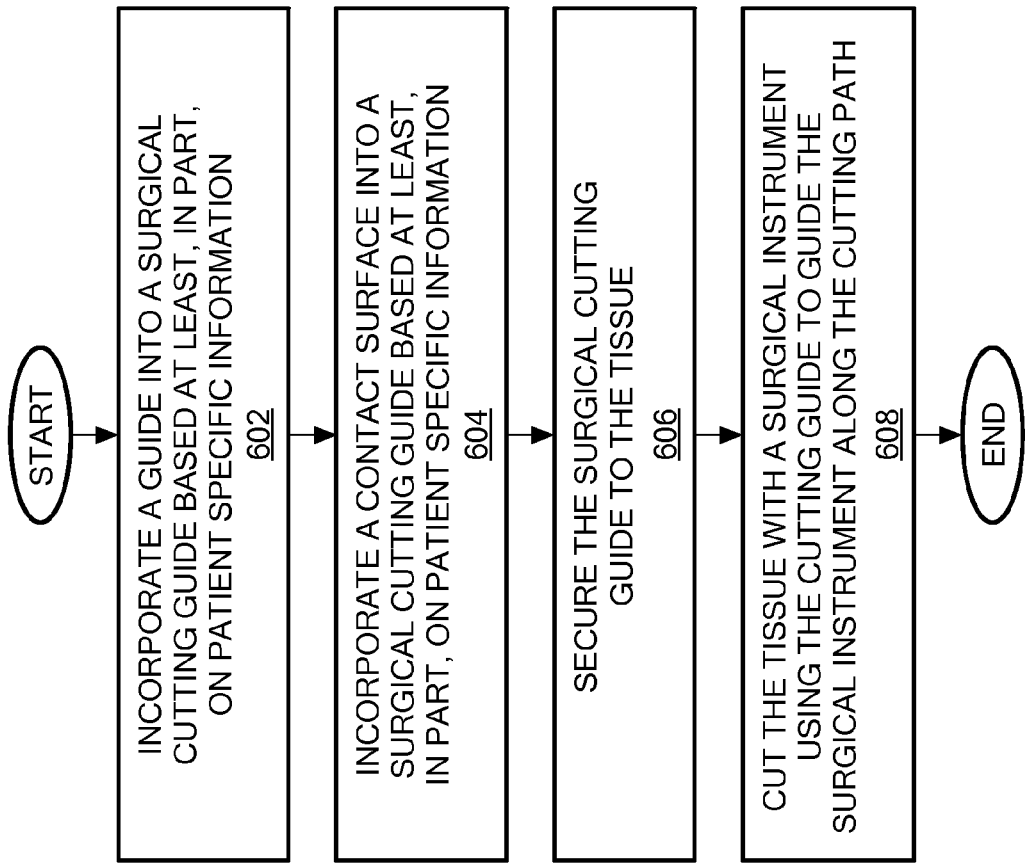
FIG. 6 depicts further examples of a method for guiding a surgical instrument, in accordance with one embodiment of the invention.
Figure 5:
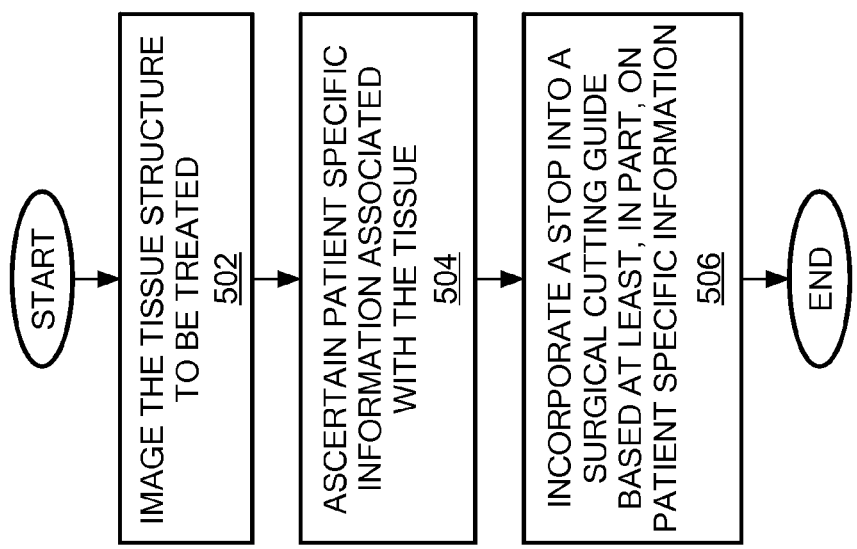
FIG. 5 depicts an example of a method for guiding a surgical instrument, in accordance with one embodiment of invention.

FIG. 5 depicts an example of a method for guiding the surgical instrument. The method may include imaging the tissue structure to be treated 502. Imaging of the tissue may be accomplished as described above through CT imaging, spiral CT imaging, MRI imaging, ultrasound scanning, digital tomosynthesis, or optical coherence tomography. Once the tissue is imaged, patient specific information is ascertained based upon the image 504. In another embodiment the patient specific information may be ascertained from intra-operative measurements of the tissue. Once the patient specific information is ascertained, the stop 116 may be incorporated into the surgical cutting guide 100 based at least, in part, on the patient specific information 506. The placement, location, orientation, and shape of the stop 116 on the cutting guide 100 may be determined based upon the surface of the tissue, the tissue structures to be preserved, the type of surgical intervention to be performed, and/or the cutting path of the surgical instrument. As depicted in FIG. 6, the placement, location, orientation, and shape of the guide 108 may also be determined based upon similar considerations and patient specific information 602. The structure of the conforming contact surface 102 may also be determined based at least, in part, on the ascertained patient specific information 604. The stop 116, the guide 108, and the contact surface 102 may be incorporated onto the cutting guide 100 as attachments to the cutting guide 100, as integral to the cutting guide 100, and/or as a single unitary structure. As discussed above, the stop 116, the guide 108, and the contact surface 102 may be molded or rapid prototyped as a single unitary structure. In another embodiment, the stop 116 may be attached onto a pre-made cutting guide 100 or template 124 that has a good fit with a patient's particular tissue structure. In yet another embodiment, the stop 116, guide 108, or contact surface 102 may be integrated into the guide through a machining process.

Once the surgical cutting guide is provided, the surgical guide 100 may be secured to the tissue 606. The conforming contact surface 102 of the surgical cutting guide 100 is placed on the mating surface of the tissue and/or adjacent tissue structures. The surgical cutting guide 100 may be secured to the tissue using the bushing holes 104, 106 and anchor screws. The surgical cutting guide 100 may also be secured to the tissue using surgical glue, bone cement, or any other appropriate fastening means. Once the surgical cutting guide 100 is secured to the tissue, the tissue may be cut with the surgical instrument using the cutting guide 100 to guide the surgical instrument along the cutting path 608. The at least one guide 108 restricts the movement of the surgical instrument in the first direction 110, but allows the movement of the surgical instrument in the second direction 112 along the cutting path across the surface of the tissue. The stop 116 restricts the movement of the surgical instrument in the second direction 112 along the cutting path. The stop 116 restricts movement of the surgical instrument in the second direction 112 by coming in contact with the surgical instrument, and more particularly, the cutting surface of the surgical instrument. After the cut is complete, the cutting guide 100 may be removed or left inside the body post-operatively depending on the particular type of surgical intervention.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A cutting guide comprising:
   a portion that substantially conforms to at least a portion of a knee joint of a patient;
   at least one guide configured to direct movement of a surgical instrument along a predetermined path; and
   a stop that prevents a surgical instrument from deviating from the predetermined path, wherein the stop includes patient-specific information derived from the knee joint of the patient including information regarding a tibial spine of the knee joint of the patient.

2. The cutting guide of claim 1, wherein the cutting guide is used for a total knee arthroplasty.

3. The cutting guide of claim 1, wherein the cutting guide is used for a partial knee arthroplasty.

4. The cutting guide of claim 1, wherein the patient-specific information further includes information regarding a shape, location or orientation of a ligament of the knee joint of the patient.

5. The cutting guide of claim 4, wherein the ligament is an anterior cruciate ligament of the knee joint.

6. The cutting guide of claim 1, wherein the portion that substantially conforms to at least a portion of the knee joint of the patient includes information derived from image data of the knee joint of the patient.

7. The cutting guide of claim 1, wherein the portion that substantially conforms to at least a portion of the knee joint of the patient includes cartilage information derived from image data of the knee joint of the patient.

8. The cutting guide of claim 1, wherein the portion that substantially conforms to at least a portion of the knee joint of the patient includes subchondral bone information derived from image data of the knee joint of the patient.

9. The cutting guide of claim 1, wherein the portion that substantially conforms to at least a portion of the knee joint of the patient includes information regarding a shape of an articular surface of the knee joint of the patient derived from image data of the knee joint of the patient.

10. The cutting guide of claim 1, wherein the portion that substantially conforms to at least a portion of the knee joint of the patient includes information regarding a shape of a non-articular surface of the knee joint of the patient derived from image data of the knee joint of the patient.

11. The cutting guide of claim 1, wherein the patient-specific information includes information regarding a shape, location or orientation of the tibial spine of the knee joint of the patient.

12. A cutting guide comprising:
a portion that substantially conforms to at least a portion of a tibia of a knee joint of a patient;
at least one guide configured to direct movement of a surgical instrument along a predetermined path; and
a stop for preventing the surgical instrument from deviating from the predetermined path, wherein the stop is integrated into the cutting guide and includes patient-specific information derived from image data of the knee joint of the patient regarding a ligament of the knee joint of the patient.

13. A cutting guide comprising:
a portion that substantially conforms to at least a portion of a tibia of a knee joint of a patient;
at least one guide configured to direct movement of a surgical instrument along a predetermined path; and
a stop for preventing the surgical instrument from deviating from the predetermined path, wherein the stop is attached to the cutting guide and includes patient-specific information derived from image data of the knee joint of the patient regarding a ligament of the knee joint of the patient.

14. The cutting guide according to claim 13, wherein the attachment is via a block.

15. The cutting guide according to claim 13, wherein the attachment of the stop is via a linkage.

16. A cutting guide comprising:
a portion that substantially matches at least a portion of a tibia of a knee joint of a patient;
at least one guide configured to direct movement of a surgical instrument along a predetermined path;
a stop for preventing the surgical instrument from deviating from the predetermined path, wherein a position, orientation or shape of the stop includes patient-specific information derived from image data of the knee joint of the patient regarding a shape or location of a tibial spine of the tibia of the knee joint of the patient.

17. The cutting guide according to claim 16, wherein the position, orientation or shape of the stop allows for intra-operative adjustments.

18. A surgical cutting guide comprising:
a surface that substantially conforms to at least a portion of a tibia of a knee joint of a patient;
at least one guide configured to direct movement of a surgical instrument along a predetermined path, wherein a position, shape or orientation of the at least one guide includes patient specific information derived from image data of the knee joint of the patient and provides for a predetermined cut angulation or a predetermined cut height and
a stop configured to restrict movement of the surgical instrument in a direction along the predetermined path, wherein the stop includes patient-specific information derived from the image data of the knee joint of the patient regarding a ligament of the knee joint of the patient.

19. The surgical cutting guide according to claim 18, wherein the predetermined cut angulation or the predetermined cut height includes patient specific information derived from image data of the knee joint of the patient.

20. A surgical cutting guide comprising:
a surface that substantially matches at least a portion of a tibia of a knee joint of a patient;
at least one guide configured to direct movement of a surgical instrument along a predetermined path; and
a stop that prevents the surgical instrument from deviating from the predetermined path wherein at least one of the shape, location, and orientation of the stop includes patient-specific information derived from image data of the joint regarding a shape, location or orientation of a a tibial spine of the knee joint of the patient to be preserved, such that the stop prevents the surgical instrument from damaging the tibial spine of the knee joint of the patient.

* * * * *